(12) United States Patent
Kalgutkar et al.

(10) Patent No.: US 7,776,940 B2
(45) Date of Patent: *Aug. 17, 2010

US007776940B2

(54) METHODS FOR REDUCING BOND STRENGTHS, DENTAL COMPOSITIONS, AND THE USE THEREOF

(75) Inventors: Rajdeep S. Kalgutkar, Woodbury, MN (US); Joan V. Brennan, Sierra Madre, CA (US); Babu N. Gaddam, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 1084 days.

This patent is subject to a terminal disclaimer.

(21) Appl. No.: 11/275,238

(22) Filed: Dec. 20, 2005

(65) Prior Publication Data

US 2007/0142497 A1 Jun. 21, 2007

(51) Int. Cl.
*C08J 3/28* (2006.01)
*C08F 2/50* (2006.01)
*C08F 2/46* (2006.01)
*A61K 6/08* (2006.01)
*A61K 6/083* (2006.01)
*A61K 6/00* (2006.01)

(52) U.S. Cl. .......... 523/116; 523/105; 523/109; 523/111; 523/112; 523/113; 523/114; 523/115; 523/118; 523/120; 522/15; 522/17; 522/25; 522/27; 522/71; 522/81; 522/77; 522/100; 522/103; 522/104; 522/107; 522/113; 522/114; 522/120; 522/908

(58) Field of Classification Search .......... 522/15, 522/17, 25, 27, 31, 71, 74–83, 100, 103, 522/104, 107, 113, 114, 120, 908; 523/105, 523/109, 111, 112, 113, 114, 115, 116, 118, 523/120
See application file for complete search history.

(56) References Cited

U.S. PATENT DOCUMENTS

| | | |
|---|---|---|
| 3,018,262 A | 1/1962 | Schroeder |
| 3,775,113 A | 11/1973 | Bonham et al. |
| 3,779,778 A | 12/1973 | Smith et al. |
| 3,954,475 A | 5/1976 | Bonham et al. |
| 3,975,422 A | 8/1976 | Buck |
| 4,094,068 A | 6/1978 | Schinhammer |
| 4,180,911 A | 1/1980 | Bullock |
| 4,200,980 A | 5/1980 | Johnston |
| 4,259,075 A | 3/1981 | Yamauchi et al. |
| 4,298,738 A | 11/1981 | Lechtken et al. |
| 4,324,744 A | 4/1982 | Lechtken et al. |
| 4,329,384 A | 5/1982 | Vesley et al. |
| 4,330,570 A | 5/1982 | Giuliani et al. |
| 4,356,296 A | 10/1982 | Griffith et al. |
| 4,385,109 A | 5/1983 | Lechtken et al. |
| 4,435,160 A | 3/1984 | Randklev |
| 4,455,138 A | 6/1984 | Sheridan |
| 4,457,818 A | 7/1984 | Denyer et al. |
| 4,499,251 A | 2/1985 | Omura et al. |
| 4,500,657 A | 2/1985 | Kumar |
| 4,503,169 A | 3/1985 | Randklev |
| 4,537,940 A | 8/1985 | Omura et al. |
| 4,539,382 A | 9/1985 | Omura et al. |
| 4,554,336 A | 11/1985 | Kidd et al. |
| 4,642,126 A | 2/1987 | Zador et al. |
| 4,648,843 A | 3/1987 | Mitra |
| 4,652,274 A | 3/1987 | Boettcher et al. |
| 4,665,217 A | 5/1987 | Reiners et al. |
| 4,673,354 A | 6/1987 | Culler |
| 4,695,251 A | 9/1987 | Randklev |
| 4,710,523 A | 12/1987 | Lechtken et al. |
| 4,737,593 A | 4/1988 | Ellrich et al. |
| 4,749,352 A | 6/1988 | Nicholson |
| 4,752,338 A | 6/1988 | Reiners et al. |
| 4,824,366 A | 4/1989 | Hohmann et al. |
| 4,872,936 A | 10/1989 | Engelbrecht |
| 4,904,183 A | 2/1990 | Hannan et al. |
| 4,920,188 A | 4/1990 | Sakashita et al. |
| 4,948,366 A * | 8/1990 | Horn et al. .......... 433/9 |
| 4,950,157 A | 8/1990 | Cleary |
| 4,952,142 A | 8/1990 | Nicholson |
| 4,978,007 A | 12/1990 | Jacobs et al. |

(Continued)

FOREIGN PATENT DOCUMENTS

DE      3836619      5/1990

(Continued)

OTHER PUBLICATIONS

Li MY et al., "Imaging by Photodecoupling of Crosslinks in Polymer Gels", Journal of Imaging Science, Society for Imaging Science and Technology, vol. 34, No. 6, Nov./Dec. 1990, pp. 259-264.
Azzeh et al., "Laser debonding of ceramic brackets: A comprehensive review," *American Journal of Orthodontics and Dentofacial Orthopedics*, Jan. 2003; 123:79-83.
Brandrup et al., Eds., *Polymer Handbook*, 4th Edition, (1999).
Buonocore et al., "A Report on a Resin Composition Capable of Bonding to Human Dentin Surfaces," *J. Dent. Res.*, 1956, 35(6):846-851.

(Continued)

*Primary Examiner*—Sanza L McClendon
(74) *Attorney, Agent, or Firm*—Kevin W. Weber

(57) ABSTRACT

Hardenable and hardened dental compositions, and articles including such hardenable and hardened compositions, are provided. In some embodiments, the hardenable dental compositions include an acid-generating component and an acid-reactive component including one or more acid-reactive groups. Upon irradiating, and optionally heating, the hardened compositions are useful, for example, for reducing the bond strength of orthodontic appliances adhered to tooth structures with the hardened compositions.

15 Claims, 3 Drawing Sheets

U.S. PATENT DOCUMENTS

| | | | |
|---|---|---|---|
| 5,008,304 A * | 4/1991 | Kmentt | 523/118 |
| 5,011,410 A | 4/1991 | Culler et al. | |
| 5,015,180 A | 5/1991 | Randklev | |
| 5,026,902 A | 6/1991 | Fock et al. | |
| 5,035,612 A | 7/1991 | Martin et al. | |
| 5,037,861 A | 8/1991 | Crivello et al. | |
| 5,040,975 A | 8/1991 | Ettwein et al. | |
| 5,062,793 A | 11/1991 | Cleary et al. | |
| 5,063,257 A | 11/1991 | Akahane et al. | |
| 5,066,231 A | 11/1991 | Oxman et al. | |
| 5,076,844 A | 12/1991 | Fock et al. | |
| 5,089,374 A | 2/1992 | Saeva | |
| 5,098,288 A | 3/1992 | Kesling | |
| 5,106,302 A | 4/1992 | Farzin-Nia et al. | |
| 5,108,285 A | 4/1992 | Tuneberg | |
| 5,110,290 A | 5/1992 | Wong | |
| 5,122,061 A | 6/1992 | Wakumoto et al. | |
| 5,130,347 A | 7/1992 | Mitra | |
| 5,141,969 A | 8/1992 | Saeva et al. | |
| 5,154,762 A | 10/1992 | Mitra et al. | |
| 5,172,809 A | 12/1992 | Jacobs et al. | |
| 5,205,734 A | 4/1993 | Marangoni et al. | |
| 5,219,283 A | 6/1993 | Farzin-Nia et al. | |
| 5,227,413 A | 7/1993 | Mitra | |
| 5,256,062 A | 10/1993 | Griott | |
| 5,263,859 A | 11/1993 | Kesling | |
| 5,269,680 A | 12/1993 | Kawaguchi | |
| 5,269,682 A | 12/1993 | Kesling | |
| 5,295,824 A | 3/1994 | Wong | |
| 5,320,532 A | 6/1994 | Farzin-Nia et al. | |
| 5,328,363 A | 7/1994 | Chester et al. | |
| 5,354,199 A | 10/1994 | Jacobs et al. | |
| 5,366,372 A | 11/1994 | Hansen et al. | |
| 5,367,002 A | 11/1994 | Huang et al. | |
| 5,393,362 A | 2/1995 | Culler | |
| 5,403,188 A | 4/1995 | Oxman et al. | |
| 5,415,544 A | 5/1995 | Oxman et al. | |
| 5,439,379 A | 8/1995 | Hansen | |
| 5,457,149 A | 10/1995 | Hall et al. | |
| 5,501,727 A | 3/1996 | Wang et al. | |
| 5,520,725 A | 5/1996 | Kato et al. | |
| 5,525,648 A | 6/1996 | Aasen et al. | |
| 5,530,038 A | 6/1996 | Yamamoto et al. | |
| 5,545,676 A | 8/1996 | Palazzotto et al. | |
| 5,554,664 A | 9/1996 | Lamanna et al. | |
| 5,569,691 A | 10/1996 | Guggenberger et al. | |
| 5,583,178 A | 12/1996 | Oxman et al. | |
| 5,635,545 A | 6/1997 | Oxman et al. | |
| 5,709,548 A | 1/1998 | Oxman et al. | |
| 5,722,826 A | 3/1998 | Tuneberg et al. | |
| 5,746,594 A | 5/1998 | Jordan et al. | |
| 5,829,972 A | 11/1998 | Farzin-Nia | |
| 5,856,373 A | 1/1999 | Kaisaki et al. | |
| 5,859,089 A | 1/1999 | Qian | |
| 5,871,360 A | 2/1999 | Kato | |
| 5,925,715 A | 7/1999 | Mitra | |
| 5,962,550 A | 10/1999 | Akahane et al. | |
| 5,965,632 A | 10/1999 | Orlowski et al. | |
| 6,030,606 A | 2/2000 | Holmes | |
| 6,084,004 A | 7/2000 | Weinmann et al. | |
| 6,089,861 A | 7/2000 | Kelly et al. | |
| 6,090,867 A | 7/2000 | Starling, Jr. et al. | |
| 6,121,362 A | 9/2000 | Wanek et al. | |
| 6,127,449 A | 10/2000 | Bissinger et al. | |
| 6,147,141 A | 11/2000 | Iyer et al. | |
| 6,159,012 A | 12/2000 | Oxman et al. | |
| 6,183,249 B1 | 2/2001 | Brennan et al. | |
| 6,187,833 B1 | 2/2001 | Oxman et al. | |
| 6,187,836 B1 | 2/2001 | Oxman et al. | |
| 6,245,828 B1 | 6/2001 | Weinmann et al. | |
| 6,251,963 B1 | 6/2001 | Köhler et al. | |
| 6,282,013 B1 | 8/2001 | Ostler et al. | |
| 6,331,080 B1 | 12/2001 | Cole et al. | |
| 6,331,343 B1 | 12/2001 | Perez et al. | |
| 6,361,721 B1 | 3/2002 | Stern | |
| 6,376,585 B1 | 4/2002 | Schofalvi et al. | |
| 6,387,981 B1 | 5/2002 | Zhang et al. | |
| 6,395,124 B1 | 5/2002 | Oxman et al. | |
| 6,395,801 B1 | 5/2002 | Bissinger et al. | |
| 6,417,244 B1 | 7/2002 | Wellinghoff et al. | |
| 6,444,725 B1 | 9/2002 | Trom et al. | |
| 6,458,868 B1 | 10/2002 | Okada et al. | |
| 6,465,541 B2 | 10/2002 | Bretscher et al. | |
| 6,474,988 B1 | 11/2002 | Georgakis et al. | |
| 6,506,816 B1 | 1/2003 | Ario et al. | |
| 6,513,897 B2 | 2/2003 | Tokie | |
| 6,528,555 B1 | 3/2003 | Nikutowski et al. | |
| 6,566,413 B1 | 5/2003 | Weinmann et al. | |
| 6,572,693 B1 | 6/2003 | Wu et al. | |
| 6,605,651 B1 | 8/2003 | Stangel et al. | |
| 6,652,970 B1 | 11/2003 | Everaerts et al. | |
| 6,669,927 B2 | 12/2003 | Trom et al. | |
| 6,670,436 B2 | 12/2003 | Burgath et al. | |
| 6,759,177 B2 | 7/2004 | Shimada et al. | |
| 6,765,036 B2 | 7/2004 | Dede et al. | |
| 6,765,038 B2 | 7/2004 | Mitra | |
| 6,825,315 B2 | 11/2004 | Aubert | |
| 6,960,079 B2 * | 11/2005 | Brennan et al. | 433/9 |
| 2002/0013382 A1 | 1/2002 | Furman et al. | |
| 2003/0035899 A1 | 2/2003 | Klettke et al. | |
| 2003/0054288 A1 | 3/2003 | Shimada et al. | |
| 2003/0099762 A1 | 5/2003 | Zhang et al. | |
| 2003/0114553 A1 | 6/2003 | Karim et al. | |
| 2003/0118970 A1 | 6/2003 | Rusin et al. | |
| 2003/0166740 A1 | 9/2003 | Mitra et al. | |
| 2003/0181541 A1 | 9/2003 | Wu et al. | |
| 2003/0195273 A1 | 10/2003 | Mitra et al. | |
| 2003/0196914 A1 * | 10/2003 | Tzou et al. | 206/63.5 |
| 2003/0198914 A1 | 10/2003 | Brennan et al. | |
| 2003/0225183 A1 | 12/2003 | De Putter et al. | |
| 2004/0026023 A1 | 2/2004 | DeMeter | |
| 2004/0151691 A1 | 8/2004 | Oxman et al. | |
| 2004/0162375 A1 | 8/2004 | Ali et al. | |
| 2004/0185013 A1 | 9/2004 | Burgio et al. | |
| 2004/0206932 A1 | 10/2004 | Abuelyaman | |
| 2005/0070627 A1 | 3/2005 | Falsafi et al. | |
| 2005/0113477 A1 | 5/2005 | Oxman et al. | |
| 2005/0133384 A1 | 6/2005 | Cinader et al. | |
| 2005/0136370 A1 | 6/2005 | Brennan et al. | |
| 2005/0182148 A1 | 8/2005 | Gaud et al. | |
| 2005/0202343 A1 | 9/2005 | Fujimaki | |
| 2005/0252413 A1 | 11/2005 | Kangas et al. | |
| 2005/0252414 A1 | 11/2005 | Craig et al. | |
| 2005/0252415 A1 | 11/2005 | Budd et al. | |
| 2005/0256223 A1 | 11/2005 | Kolb et al. | |

FOREIGN PATENT DOCUMENTS

| | | | |
|---|---|---|---|
| EP | 0 037 677 A2 | 10/1981 | |
| EP | 0 037 677 A3 | 10/1981 | |
| EP | 0 173 567 A2 | 3/1986 | |
| EP | 0 173 567 A3 | 3/1986 | |
| EP | 0 237 233 A2 | 9/1987 | |
| EP | 0 237 233 A3 | 9/1987 | |
| EP | 0 037 677 B1 | 11/1988 | |
| EP | 0 296 384 A2 | 12/1988 | |
| EP | 0 296 384 A3 | 12/1988 | |
| EP | 0 373 384 | 6/1990 | |
| EP | 0 712 622 A1 | 5/1996 | |
| EP | 0 712 622 B1 | 9/1999 | |
| EP | 1 004 279 A1 | 5/2000 | |
| EP | 1 051 961 A1 | 11/2000 | |
| EP | 1 169 995 A1 | 1/2002 | |
| EP | 1 228 744 A2 | 8/2002 | |

| | | | |
|---|---|---|---|
| EP | 1 228 744 A3 | 8/2002 |
| EP | 1 352 617 A1 | 10/2003 |
| EP | 1 475 069 A1 | 11/2004 |
| EP | 1 004 279 B1 | 7/2005 |
| EP | 1 228 744 B1 | 8/2005 |
| EP | 1 051 961 B1 | 2/2006 |
| JP | 5-85912 | 4/1993 |
| JP | 5-170619 | 7/1993 |
| JP | 5-245167 | 9/1993 |
| JP | 9-2916 | 1/1997 |
| WO | WO 87/01577 A1 | 3/1987 |
| WO | WO 94/22972 A1 | 10/1994 |
| WO | WO 98/01103 A1 | 1/1998 |
| WO | WO 98/09913 A1 | 3/1998 |
| WO | WO 00/38619 A2 | 7/2000 |
| WO | WO 00/38619 A3 | 7/2000 |
| WO | WO 00/42092 A1 | 7/2000 |
| WO | WO 00/69393 A1 | 11/2000 |
| WO | WO 01/07444 A1 | 2/2001 |
| WO | WO 01/30305 A1 | 5/2001 |
| WO | WO 01/30306 A1 | 5/2001 |
| WO | WO 01/30307 A1 | 5/2001 |
| WO | WO 01/51540 A2 | 7/2001 |
| WO | WO 01/51540 A3 | 7/2001 |
| WO | WO 01/92271 A1 | 12/2001 |
| WO | WO 02/30363 | 4/2002 |
| WO | WO 02/092021 A1 | 11/2002 |
| WO | WO 03/031492 A1 | 4/2003 |
| WO | WO 03/063804 A1 | 8/2003 |
| WO | WO 2004/002361 | 1/2004 |
| WO | WO 2004/060327 | 4/2004 |
| WO | WO 2005/018581 A2 | 3/2005 |
| WO | WO 2005/018581 A3 | 3/2005 |
| WO | WO 2006/020760 A1 | 2/2006 |
| WO | WO 2007/075257 | 4/2007 |
| WO | WO 2007/075663 | 4/2007 |
| WO | WO 2007/075705 | 4/2007 |

OTHER PUBLICATIONS

Craig and Ward, Eds., *Restorative Dental Materials*, Tenth Edition, Mosby-Year Book, Inc., St. Louis, MO, Chapter 11 (Impression Mateirals), (1997).

Crivello et al., *Photoinitiators for Free Radical, Cationic & Anionic Photopolymerization*, vol. 3, $2^{nd}$ Edition, G. Bradley, Editor, Title page, publication page, Table of contents, and Chapter III (pp. 329-478) (1998).

Demus et al., Eds., *Liquid Crystals Handbook*, vols. 1-3 (1998).

Greene et al., *Protective Groups in Organic Synthesis*, Wiley-Intersciences (1999).

Lee and Neville, *Handbook of Epoxy Resins*, McGraw-Hill Book Co., New York (1967).

Laufer et al., "Numerical Analysis of the Thermochemical Tooth Damage Induced by Laser Radiation," *Journal of Biomechanical Engineering*, Aug. 1985; 107:234-239.

Launay et al., "Thermal Effects of Laser on Dental Tissues," *Lasers in Surgery and Medicine*, 7:473-477 (1987).

Mathis et al., "Properties of a New Glass Ionomer/Composite Resin Hybrid Restorative," Abstract No. 51, *J. Dent. Res.*, 66:113 (1987).

Matsuoka, Ed., *Infrared Absorbing Dyes*, Plenum Press, New York (1990).

Rudin, *The Elements of Polymer Science and Engineering*, $2^{nd}$ Edition, Chapter 11, Title page, Publication page, and pp. 377-443 (1999).

Smith et al., *March's Advanced Organic Chemistry: Reactions, Mechanisms, and Structure*, Wiley (2001).

Taylor et al., "Positive, Chemically Amplified Aromatic Methacrylate Resist Employing the Tetrahydropyranyl Protecting Group," *Chem. Mater.*, 1991; 3(6):1031-1040.

Uysal et al., *Angle Orthodontist*, 75:220-225 (2005).

Zach et al., "Pulp response to externally applied heat," *Endodontics*, Bender, Ed., pp. 515-530 (1965).

Rickabaugh, J. Marangoni R., McCaffrey K. Ceramic bracket debonding with the carbon dioxide laser. American Journal of Orthodontics and Dentofacial Orthopedics 1996; 110:388-393.

\* cited by examiner

US 7,776,940 B2

METHODS FOR REDUCING BOND STRENGTHS, DENTAL COMPOSITIONS, AND THE USE THEREOF

BACKGROUND

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to use adhesives to bond orthodontic appliances to the surface of the tooth, using either direct or indirect methods. A variety of adhesives are available to the practitioner for bonding brackets to tooth surfaces, and many offer excellent bond strengths. High bond strengths are desirable for maintaining adhesion of the bracket to the tooth surface over the duration of the treatment process, which can typically be two years or more.

However, orthodontic adhesives with high bond strengths can lead to other difficulties. For example, one of the most difficult aspects of the orthodontic treatment process can be the removal of the bracket after completion of treatment. It is well known in the industry that certain adhesives, used in combination with certain rigid brackets, are capable of causing enamel fracture under some debonding conditions. As a result, many commercially available ceramic brackets have been designed for the bond to fail at the interface between the bracket and the adhesive to prevent damage to the tooth surface during the debonding process. However, this approach results in most of the cured adhesive pad being left behind on the tooth surface after the bracket has been removed. Removal of the adhesive pad, which is typically hard and heavily crosslinked, can be time consuming for the clinician and uncomfortable for the patient.

New adhesives and methods are needed that offer satisfactory adhesion of the bracket to the tooth surface throughout the treatment process, and also allow for more convenient removal upon completion of the treatment.

SUMMARY OF THE INVENTION

In one aspect, the present invention provides a method for reducing the adherence of a hardened dental composition to a tooth structure. The method includes irradiating the hardened dental composition to reduce the adherence, wherein the hardened dental composition includes an acid-generating component and an acid-reactive component having one or more acid-reactive groups.

In another aspect, the present invention provides a method for reducing the bond strength of an orthodontic appliance adhered to a tooth structure with a hardened dental composition (e.g., a hardened orthodontic adhesive, a hardened orthodontic cement, and/or a hardened primer) that includes an acid-generating component and an acid-reactive component having one or more acid-reactive groups. In one embodiment, the method includes irradiating the hardened dental composition to reduce the bond strength. Optionally, the method further includes heating at least a portion of the hardened dental composition to at least 42° C. Preferably, the hardened dental composition maintains sufficient bond strength prior to irradiation (e.g., throughout the duration of the treatment), but provides reduced bond strength upon irradiation, and optionally heating, to allow for convenient removal of the orthodontic appliance from the tooth structure (e.g., less force required to debond the appliance). In some embodiments, the dental composition including the acid-generating component and the acid-reactive component can be placed so as to result in fracture (e.g., adhesive failure) upon debonding at an interface (e.g., an adhesive-tooth interface or an appliance-adhesive interface), or cohesive failure within the hardened dental composition upon debonding. For example, fracture at an adhesive-tooth interface can result in the hardened adhesive being substantially retained on the removed orthodontic appliance, providing for convenient clean-up of the tooth structure.

In still another aspect, the present invention provides a method for reducing the bond strength of an orthodontic appliance adhered to a tooth structure with a hardened dental composition. The method includes irradiating the hardened dental composition and subsequently heating the irradiated hardened dental composition, resulting in a reduced bond strength.

In yet another aspect, the present invention provides a hardenable dental composition that includes a hardenable component having one or more acid-reactive groups and an acid-generating component, and/or articles (e.g., orthodontic appliances) having the hardenable dental composition thereon. Optionally, such articles having the hardenable dental composition thereon are provided as precoated articles. In some embodiments, the hardenable component having one or more acid-reactive groups is an ethylenically unsaturated compound. Optionally, the hardenable dental composition (e.g., an orthodontic primer or an orthodontic adhesive) further includes a hardenable component without an acid-reactive group (e.g., an ethylenically unsaturated compound), an initiator for initiating hardening of the dental composition, a sensitizer, and/or a filler. Optionally, articles having the hardenable and/or hardened dental composition thereon can additionally include one or more layers of different hardenable and/or hardened dental compositions. Methods for making and using such hardenable dental compositions, and/or articles having such hardenable and/or hardened dental compositions thereon, are also provided.

Definitions

As used herein, "dental composition" refers to a material (e.g., a dental or orthodontic material) capable of adhering (e.g., bonding) to a tooth structure. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives, liners, sealants (e.g., orthodontic sealants), and coatings. Oftentimes a dental composition can be used to bond a dental article to a tooth structure.

As used herein, "dental article" refers to an article that can be adhered (e.g., bonded) to a tooth structure. Dental articles include, for example, crowns, bridges. veneers, inlays, onlays, fillings, orthodontic appliances and devices, and prostheses (e.g., partial or full dentures).

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e., single or multi-layer adhesives).

As used herein, a "packaged" article refers to an orthodontic appliance or card that is received in a container. Preferably, the container provides protection from environmental conditions including, for example, moisture and light.

As used herein, a "release" substrate refers to a substrate in contact with an article that is removed from the article before or during use of the article.

As used herein, a "radiation-to-heat converter" refers to a material or composition that absorbs incident radiation (e.g., visible light, ultraviolet (UV) radiation, infrared (IR) radiation, near infrared (NIR) radiation, and/or radio frequency (RF) radiation) and converts a substantial portion (e.g., at least 50%) of the incident radiation into heat, which can be useful for softening the thermally responsive additive.

As used herein, "softening" refers to loss of modulus of a material that can occur as a result of physical and/or chemical changes in the material. The degree of softness or deformability of a material is sometimes referred to as "compliance" of the material, wherein compliance is defined as the inverse of the Young's modulus of the material.

As used herein, "tooth structure" refers to surfaces including, for example, natural and artificial tooth surfaces, bone, tooth models, and the like.

As used herein, a "multi-layer" adhesive refers to an adhesive having two or more distinctly different layers (i.e., layers differing in composition, and preferably having different chemical and/or physical properties).

As used herein, a "layer" refers to a discontinuous (e.g., a patterned layer) or continuous (e.g., non-patterned) material extending across all or a portion of a material different than the layer. The layer may be of uniform or varying thickness.

As used herein, a "patterned layer" refers to a discontinuous material extending across (and optionally attached to) only selected portions of a material different than the patterned layer.

As used herein, a "non-patterned layer" refers to a continuous material extending across (and optionally attached to) an entire portion of a material different than the non-patterned layer.

In general, a layer "on," "extending across," or "attached to" another material different than the layer is intended to be broadly interpreted to optionally include one or more additional layers between the layer and the material different than the layer.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked) or solidified.

As used herein, "hardener" refers to something that initiates hardening of a resin. A hardener may include, for example, a polymerization initiator system, a photoinitiator system, and/or a redox initiator system.

As used herein, "photobleachable" refers to loss of color upon exposure to actinic radiation.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution. As used herein, "a" or "an" means one or more.

DETAILED DESCRIPTION OF CERTAIN EMBODIMENTS

Figure 1:
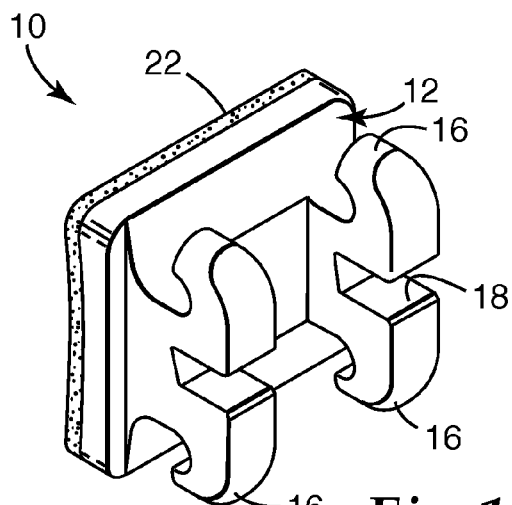
FIG. 1 is perspective view of an orthodontic appliance having a hardenable or hardened dental composition of the present invention on the base thereof.

The present invention provides hardenable dental compositions, and articles including such compositions, that are capable of adhering to a tooth structure upon hardening. Further, the adherence (e.g., bond strength) to the tooth structure of such hardened compositions can be reduced upon irradiating, and optionally heating, typically under convenient conditions. The reduced adherence can be useful if and when it is desired to remove the hardened composition from the tooth structure. Such hardenable dental compositions encompass materials (e.g., dental and/or orthodontic materials) capable of adhering (e.g., bonding) to a tooth structure, such as adhesives (e.g., dental and/or orthodontic adhesives), cements (e.g., glass ionomer cements, resin-modified glass ionomer cements), primers, restoratives, liners, sealants, and coatings. Oftentimes a dental composition can be used to bond a dental article (e.g., an orthodontic appliance) to a tooth structure.

In some embodiments, such hardenable dental compositions can, upon hardening, provide sufficient bond strength to adhere an orthodontic appliance to a tooth structure during orthodontic treatment, and are further useful for reducing the bond strength, for example, at the end of the treatment process when it is necessary for the practitioner to remove the appliance from the tooth structure. The compositions, articles, and methods are designed to reduce the bond strength upon irradiating, and optionally heating, of the hardened dental composition under convenient conditions. The resulting reduced bond strength can allow for convenient removal of not only the orthodontic appliance, but also for any hardened dental composition remaining on the tooth structure after removal of the appliance.

In some embodiments, hardenable and hardened dental compositions of the present invention include an acid-generating component and an acid-reactive component, which are described in detail herein. As used herein, an "acid-generating component" typically includes an acid-generating compound, and optionally a sensitizer. Preferably, the acid-generating component generates an acid upon irradiation (i.e., a photo-acid). As used herein, an "acid-reactive component" refers to a component (typically a compound) that includes one or more acid-reactive groups. As used herein, an "acid-reactive group" refers to a group that undergoes, after reaction with an acid, substantial breaking of chemical bonds within the group to form two or more separate groups, often upon heating to an elevated temperature (i.e., at least 42° C.).

Acid-generating components and acid-reactive components can be incorporated into a wide variety of dental compositions (e.g., dental and orthodontic materials) including, for example, adhesives, cements (e.g., glass ionomer cements, resin-modified glass ionomer cements), primers, restoratives, liners, sealants, and coatings at levels effective to decrease bond strength of the hardened composition upon irradiating, and optionally heating, while maintaining sufficient adhesion (e.g., of an orthodontic appliance) to the tooth structure during treatment. Treatment can include dental and/or orthodontic treatment processes that last a month, a year, two years, or even longer.

For certain embodiments, such dental compositions can be conveniently applied to the base of an orthodontic appliance by a practitioner. Alternatively, orthodontic appliances can be provided having such dental compositions precoated on the base of the appliance. Typically such precoated appliances are provided as packaged articles with or without a release liner or foam pad liner such as those described, for example, in U.S. Pat. No. 6,183,249 (Brennan et al.). Exemplary containers are well known in the art and are disclosed, for example, in U.S. Pat. No. 5,172,809 (Jacobs et al.) and U.S. Pat. No. 6,089,861 (Kelly et al.).

Hardenable dental compositions of the present invention typically include an ethylenically unsaturated compound, an initiator, an acid-generating component, and an acid-reactive component. The acid-reactive component can optionally be a hardenable component. In some embodiments, the hardenable dental composition also includes a filler. In some embodiments, the hardenable dental composition further includes an ethylenically unsaturated compound with acid functionality, wherein the hardenable dental composition can be, for example, a self-etching orthodontic primer or a self-etching orthodontic adhesive. In some embodiments, the hardenable dental composition further includes a radiation-to-heat converter as described hereinafter. Optionally, the hardenable dental composition of the present invention can include a thermally labile component and/or a thermally responsive additive as described hereinafter. Preferably, such compositions, upon hardening, can bond an orthodontic appliance to a tooth structure with a bond strength (using the shear peel test method described herein) of at least 7 MPa at room temperature.

Acid-Generating Component

In some embodiments, hardenable dental compositions of the present invention include an acid-generating component. Acid-generating components typically include an acid-generating compound, and optionally a sensitizer. Preferably, the acid-generating component generates an acid upon irradiation (i.e., a photo-acid). Typically, the acid can react with greater than a stoichiometric amount of acid-reactive groups. Preferably, dental compositions of the present invention do not include groups that would act to deplete the generated acid in amounts sufficient to interfere with the desired reaction of the generated acid with the acid-reactive component.

Exemplary acid-generating components include iodonium salts (e.g., diaryliodonium salts), sulfonium salts (e.g., triarylsulfonium salts and dialkylphenacylsulfonium salts), selenonium salts (e.g., triarylselenonium salts), sulfoxonium salts (e.g., triarylsulfoxonium salts, aryloxydiarylsulfoxonium salts, and dialkylphenacylsulfoxonium salts), diazonium salts (e.g., aryldiazonium salts), organometallic complex cations (e.g., ferrocenium salts), halo-S-triazenes, trihaloketones, α-sulfonyloxy ketones, silyl benzyl ethers, and combinations thereof. When the acid-generating component is a salt of a cationic species (e.g., an "onium" salt), typical counterions for the salt include, for example, tetrafluoroborate, hexafluorophosphate, hexafluoroarsenate, hexafluoroantimonate, and combinations thereof. Exemplary acid-generating components include those disclosed, for example, in Crivello et al., "Photoinitiators for Free Radical, Cationic and Anionic Photopolymerization," G. Bradley, Editor, Volume 3, Chapter 6 (1998), and U.S. Pat. No. 6,187,833 (Oxman et al.), U.S. Pat. No. 6,395,124 (Oxman et al.), U.S. Pat. No. 6,765,036 (Dede et al.), U.S. Pat. No. 3,775,113 (Bonham et al.), U.S. Pat. No. 3,779,778 (Smith et al.), U.S. Pat. No. 3,954,475 (Bonham et al.), U.S. Pat. No. 4,329,384 (Vesley et al.), U.S. Pat. No. 4,330,570 (Giuliani et al.), U.S. Pat. No. 5,089,374 (Saeva), and U.S. Pat. No. 5,141,969 (Saeve et al.).

Preferably the acid-generating component includes a sulfonium salt. Exemplary sulfonium salts include, for example, triaryl sulfonium hexafluoroantimonate ($Ar_3S^+$ $SbF_6^-$, available under the trade designation CYRACURE CPI-6976 from Advanced Research Corporation, Catoosa, Okla.); triaryl sulfonium hexafluorophosphate ($Ar_3S^+$ $PF_6^-$, 50% solution in propylene carbonate, available under the trade designation CYRACURE CPI-6992, from Aceto Corp., Lake Success, N.Y.); and triaryl sulfonium N-(trifluoromethanesulfonyl)trifluoromethane-sulfonamido anion ($Ar_3S^+$ $N(SO_2CF_3)_2)^-$, which can be prepared as generally described in U.S. Pat. No. 5,554,664 (Lamanna et al.).

Exemplary sensitizers include anthracene derivatives (e.g., 2-methylanthracene (2-MA, Sigma-Aldrich) and 2-ethyl-9,10-dimethoxyanthracene (EDMOA, Sigma-Aldrich)), perylene, phenothiazene, and other polycyclic aromatic compounds as described, for example, in U.S. Pat. No. 6,765,036 (Dede et al.) and U.S. Pat. Publication No. 2005/0113477 (Oxman et al.), and combinations thereof. One of skill in the art could select, without undue experimentation, an appropriate sensitizer for sensitizing a specific acid-generating component (e.g., a sulfonium salt) based on the principles described, for example, in Crivello et al., "Photoinitiators for Free Radical, Cationic and Anionic Photopolymerization," G. Bradley, Editor, Volume 3, Chapter 6 (1998). Preferably, a sensitizer can be selected that absorbs at a different wavelength than the photoinitiator; has a singlet or triplet state that is higher in energy than the corresponding singlet or triplet state in the acid-generating component; and/or has an oxidation potential such that reduction of the acid-generating component is energetically favorable. For example, 2-methylanthracene is an appropriate sensitizer for sensitizing triaryl sulfonium hexafluoroantimonate.

Acid-generating components can preferably be incorporated into dental compositions of the present invention at levels effective to decrease the bond strength of the hardened dental composition upon irradiating, and optionally heating to the desired temperature. Preferably, such levels of acid-generating components also allow for sufficient adhesion during treatment process. Although levels of acid-generating components will depend on the specific dental composition being used, typically the hardenable dental composition will include at least 0.01%, preferably at least 0.1%, 1%, 3%, or even 10% by weight of an acid-generating component, based on the total weight of the dental composition.

Dental compositions can optionally include a small amount of base (less than 1 equivalent, and preferably less than 0.1 equivalent, based on equivalents of acid-generating component) to minimize premature degradation of the acid-reactive component. Exemplary bases include triethylamine, triethanolamine, 1,4-diazabicyclo[2.2.2]octane (DABCO), ethyl (4-dimethylamino)benzoate (EDMAB) and other electron donors for photoinitiator systems, bases including a polymerizable group such as 2-aminoethylmethacrylate, and combinations thereof. If base is present, typically the dental composition includes at least 0.01%, 0.1%, 1%, or even 5% by weight of base, based on the total weight of the dental composition.

Acid-generating components are typically dissolved, dispersed, or suspended in, for example, one or more ethylenically unsaturated compounds to form the dental composition.

Acid-Reactive Components

In some embodiments, hardenable dental compositions of the present invention include acid-reactive components. As used herein, an "acid-reactive component" refers to a component (typically a compound) that includes one or more acid-reactive groups. As used herein, an "acid-reactive group" refers to a group that undergoes, after reaction with an acid, substantial breaking (e.g., observable by spectroscopic techniques) of chemical bonds within the group to form two or more separate groups, often upon heating to an elevated temperature (i.e., at least 42° C.). Preferably, the elevated temperature is no greater than 200° C., more preferably no greater than 150° C., and even more preferably no greater than 100° C., and most preferably no greater than 80° C. Suitable methods for determining whether substantial breaking of chemical bonds occurs after reaction of a component with an acid would be apparent to one of skill in the art. Suitable methods include, for example, spectroscopic methods such as nuclear magnetic resonance (NMR) spectroscopy (including $^1$H, $^{13}$C, and/or other appropriate nuclei); and ultraviolet (UV), visible, and infrared (IR) spectroscopy, including near IR (NIR) spectroscopy. For example, $^1$H and/or $^{13}$C NMR spectra can be conveniently run in an NMR tube by dissolving the component in a non-acidic solvent (e.g., CDCl$_3$), adding an acid (e.g., CF$_3$CO$_2$D), and observing the disappearance of peaks arising from the component or the appearance of peaks arising from a reaction product at the desired temperature.

In certain embodiments, a hardened dental composition including an acid-generating component and an acid-reactive component softens to a greater extent than the hardened dental composition not including an acid-generating component and an acid-reactive component, upon irradiating and heating to a temperature (e.g., no greater than 200° C., preferably no greater than 150° C., more preferably no greater than 100° C., and most preferably no greater than 80° C.). The temperature at which substantial softening begins to occur (e.g., the "trigger" temperature) can be varied, for example, by selection of the pKa of the acid generated by the acid-generating component, as well as the concentration of the acid generated. Specifically, upon irradiating and heating to an elevated temperature (i.e., at least 42° C.), the storage modulus of the hardened dental composition at the elevated temperature decreases compared to the storage modulus of the hardened dental composition not including the an acid-generating component and an acid-reactive component at the same elevated temperature. Preferably, the storage modulus of the dental composition at the elevated temperature is at most 60%, more preferably at most 40%, 20%, 10%, 5%, 1%, 0.1%, or even 0.01% of the storage modulus of the hardened dental composition not including the acid-generating component and the acid-reactive component at the same elevated temperature.

Typically and preferably, a hardened dental composition including an acid-generating component and an acid-reactive component shows lower bond strength, upon irradiation and at an elevated temperature (e.g., no greater than 200° C., preferably no greater than 150° C., more preferably no greater than 100° C., and most preferably no greater than 80° C.). Specifically, upon irradiation and heating to an elevated temperature (i.e., at least 42° C.), the bond strength of the hardened dental composition at the elevated temperature decreases compared to the bond strength of the hardened dental composition not including the an acid-generating component and an acid-reactive component at the same elevated temperature. Preferably, the bond strength of the dental composition at the elevated temperature (e.g., 70° C.) is at most 90%, more preferably at most 80%, 50%, 30%, 20%, or even 10% of the bond strength of the hardened dental composition not including the an acid-generating component and an acid-reactive component at the same elevated temperature (e.g., 70° C.). Further, in certain embodiments it is preferred that bond strengths at the elevated temperature be maintained at a sufficient level (e.g., to avoid having brackets fall off into the patient's mouth before pressure is applied by the practitioner). In such embodiments, it is preferred that the bond strength of the dental composition at the elevated temperature (e.g., upon exposure to hot foods) is at least 6 MPa at the elevated temperature.

Preferably, dental compositions including at most 50%, more preferably at most 30%, 20%, 10%, 5%, or even 1% by weight loading of the acid-reactive component can exhibit such losses in bond strength at an elevated temperature. Further, at the same loadings of acid-reactive component, preferably the bond strength of the hardened dental composition at room temperature (e.g., 25° C.) is at least 50%, more preferably at least 70%, 90%, 100%, or even greater than 100% of the bond strength of the hardened dental composition not including the acid-reactive component at the same temperature.

Acid-reactive components suitable for use in hardenable dental compositions of the present invention are preferably hardenable components that include one or more acid-reactive groups. Typically, each acid-reactive group is a multivalent group linking a plurality (i.e., two or more) of hardenable groups. In certain embodiments, the hardenable acid-reactive component is an ethylenically unsaturated compound. For example, in such embodiments, the acid-reactive group can be a divalent group linking two ethylenically unsaturated groups.

Acid reactive groups are well known in the art. Such groups include, for example, functionalities typically used in protection methodologies in organic synthesis, where the protecting group can be designed for removal under acidic conditions. See, for example, Greene et al. *Protective Groups in Organic Synthesis*, Wiley-Interscience (1999); Taylor et al., *Chem. Mater.*, 3:1031-1040 (1991); and U.S. Pat. No. 6,652,970 (Everaerts et al.).

In one embodiment, the acid-reactive component includes a carbonic ester group. Exemplary acid-reactive components including a carbonic ester group can be represented by the formula (Formula I):

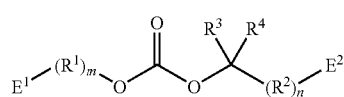

wherein $R^1$ and $R^2$ each independently represent an organic group that can optionally include one or more carbonic esters;

$R^3$ and $R^4$ each independently represent hydrogen or an organic group, with the proviso that only one of $R^3$ and $R^4$ can be hydrogen; each $E^1$ and $E^2$ independently represents an ethylenically unsaturated group; and m and n are each independently 0 or 1. $R^1$ and $E^1$ can optionally be combined to form one or more rings and/or two or more groups among $R^2$, $R^3$, $R^4$, and $E^2$ can optionally be combined to form one or more rings.

In certain embodiments, $R^1$ and $R^2$ each independently represent a C1 to C10 organic group (e.g., a C1 to C10 aliphatic group, and sometimes a C1 to C10 aliphatic moiety). In certain embodiments, $R^3$ and $R^4$ each independently represent hydrogen or a C1-C10 organic group (e.g., a C1 to C10 aliphatic group, and sometimes a C1 to C10 aliphatic moiety), with the proviso that only one of $R^3$ and $R^4$ can be hydrogen.

As used herein, an "ethylenically unsaturated group" refers to a group that includes one or more ethylenic unsaturations. Thus, an ethylenically unsaturated group can include other substituents in addition to the one or more ethylenic unsaturations. Each $E^1$ and $E^2$ can independently represent an ethylenically unsaturated group (i.e., a group containing a carbon-carbon double bond) selected from a wide variety of ethylenically unsaturated groups including, for example, (meth)acryloyl groups, vinyl groups (including styryl groups such as divinyl benzene groups), allyl groups, and combinations thereof.

In another embodiment, the acid-reactive component includes an acetal group. Exemplary acid-reactive components including an acetal group can be represented by the formula (Formula II):

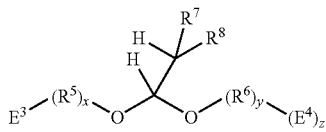

wherein $R^5$, $R^6$, $R^7$, and $R^8$ each independently represent an organic group that can optionally include one or more acetals; each $E^3$ and $E^4$ independently represents an ethylenically unsaturated group (as defined herein above); and x, y, and z are each independently 0 or 1, with the proviso that if z=0, then at least one of $R^7$ and $R^8$ represents an ethylenically unsaturated group, with $R^5$ and $R^6$ being selected such that at least a portion of the oxygen atoms attached to $R^5$ are cleaved from the acetal upon exposure to acid. In certain embodiments, the oxygen atom attached to $R^5$ is preferentially cleaved from the acetal compared to the oxygen atoms attached to $R^6$. For example, $R^5$ can be selected to be an electron donating group to increase the electron density on the oxygen atom attached to $R^5$, and/or $R^6$ can be selected to be an electron withdrawing group to decrease the electron density on the oxygen atom attached to $R^6$ to provide for the desired cleavage from the acetal of the oxygen atom attached to $R^5$. Two or more of $R^5$, $R^6$, $R^7$, $R^8$, $E^3$, and/or $E^4$ can optionally be combined to form one or more rings, with the proviso that the one or more rings do not interfere with the ability of the acid-reactive group to form two or more separate groups upon reaction with acid.

As used herein, the term "electron donating group" refers to a group that can donate electrons. Suitable examples include, for example, groups that contain amino functionality (e.g., primary amino, secondary amino, and/or tertiary amino), hydroxy functionality, alkoxy functionality, aryloxy functionality, alkyl functionality, and combinations thereof.

If an electron donating group is present, preferably $R^5$ includes the electron donating functionality in the alpha position (e.g., attached to a carbon of $R^5$ attached to the oxygen atom).

As used herein, the term "electron withdrawing group" refers to a group that can withdraw electrons. Suitable examples include, for example, groups that contain halo functionality, cyano functionality, fluoroalkyl functionality, perfluoroalkyl functionality, carboxy functionality, alkoxycarbonyl functionality, aryloxycarbonyl functionality, halocarbonyl functionality, formyl functionality, carbonyl functionality, sulfo functionality, alkoxysulfonyl functionality, aryloxysulfonyl functionality, perfluoroalkylsulfonyl functionality, alkylsulfonyl functionality, azo functionality, alkenyl functionality, alkynyl functionality, dialkylphosphonato functionality, diarylphosphonato functionality, and combinations thereof. If an electron withdrawing group is present, preferably $R^6$ includes the electron withdrawing functionality in the alpha position (e.g., attached to a carbon of $R^6$ attached to the oxygen atom).

In certain embodiments, $R^5$, $R^6$, $R^7$, and $R^8$ each independently represent a C1 to C10 organic group (e.g., a C1 to C10 aliphatic group, and sometimes a C1 to C10 aliphatic moiety).

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable groups are those that do not interfere with the hardening of the dental composition or the long-term aging of the adhesive. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" (e.g., "organic group" and "organic moiety") are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, amino, carboxyl, etc. Thus, "alkyl group" includes ether groups, haloalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Acid-reactive components can preferably be incorporated into dental compositions of the present invention at levels effective to decrease the bond strength of the hardened dental composition upon irradiating, and optionally heating to the desired temperature. Acid-reactive components are typically dissolved, dispersed, or suspended in, for example, one or more ethylenically unsaturated compounds to form the dental composition. Preferably, such levels of the acid-reactive component also allow for sufficient adhesion during treatment process. Although levels of acid-reactive component will depend on the specific dental composition being used, typically the hardenable dental composition will include at least 5%, preferably at least 10%, 20%, 30%, or even 50% by weight acid-reactive component, based on the total weight of the dental composition. Typically, the dental composition will include at most 95%, preferably at most 90%, 80%, 70%, or even 50% by weight acid-reactive component, based on the total weight of the dental composition.

Acid-reactive components are typically dissolved, dispersed, or suspended in, for example, one or more ethylenically unsaturated compounds to form the dental composition.

In some embodiments, the acid-generating component and/or the acid-reactive component are distributed uniformly throughout the hardenable and/or hardened dental composition. In other embodiments, especially for embodiments in which the hardenable dental composition is precoated on the base of an orthodontic appliance, the acid-generating component and/or the acid-reactive component can be concentrated in a portion of the hardenable dental composition. For example, the acid-generating component and/or the acid-reactive component can be concentrated near one surface (e.g., the outer surface that will contact the tooth structure) to influence the fracture to occur near the tooth structure upon debonding. Acid-generating component and/or acid-reactive component concentrated near one surface is meant to include acid-generating component and/or acid-reactive component adhered to a surface of the hardenable or hardened dental composition.

Hardenable Component

The hardenable dental compositions of the present invention typically include a hardenable (e.g., polymerizable) component (which can optionally be the acid-reactive component), thereby forming hardenable (e.g., polymerizable) compositions. The hardenable component can include a wide variety of chemistries, such as ethylenically unsaturated compounds (with or without acid functionality, and preferably without acid functionality), epoxy (oxirane) resins, vinyl ethers, photopolymerization systems, redox cure systems, glass ionomer cements, polyethers, polysiloxanes, and the like. In some embodiments, the compositions can be hardened (e.g., polymerized by conventional photopolymerization and/or chemical polymerization techniques) prior to applying the hardened dental composition. In other embodiments, a dental composition can be hardened (e.g., polymerized by conventional photopolymerization and/or chemical polymerization techniques) after applying the dental composition.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions of the present invention include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

Ethylenically Unsaturated Compounds

The compositions of the present invention may include one or more hardenable components in the form of ethylenically unsaturated compounds with or without acid functionality, thereby forming hardenable compositions.

Suitable hardenable compositions may include hardenable components (e.g., photopolymerizable compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

The compositions (e.g., photopolymerizable compositions) may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The hardenable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired.

Preferably, compositions of the present invention include at least 5% by weight, more preferably at least 10% by weight, and most preferably at least 15% by weight ethylenically unsaturated compounds, based on the total weight of the unfilled composition. Preferably, compositions of the present invention include at most 95% by weight, more preferably at most 90% by weight, and most preferably at most 80% by weight ethylenically unsaturated compounds, based on the total weight of the unfilled composition.

Preferably, compositions of the present invention include ethylenically unsaturated compounds without acid functionality. Preferably, compositions of the present invention include at least 5% by weight (wt-%), more preferably at least 10% by weight, and most preferably at least 15% by weight ethylenically unsaturated compounds without acid functionality, based on the total weight of the unfilled composition. Preferably, compositions of the present invention include at most 95% by weight, more preferably at most 90% by weight, and most preferably at most 80% by weight ethylenically unsaturated compounds without acid functionality, based on the total weight of the unfilled composition.

Ethythylenically Unsaturated Compounds with Acid Functionality

The compositions of the present invention may include one or more hardenable components in the form of ethylenically unsaturated compounds with acid functionality, thereby forming hardenable compositions.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include compositions that include combinations of ethylenically unsaturated compounds with acid functionality. Preferably the compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth) acryloxy group are linked together by a C1-C4 hydrocarbon group; a second compound including at least one (meth) acryloxy group and at least one —O—P(O)(OH)$_x$ group, wherein x=1 or 2, and wherein the at least one —O—P(O) (OH)$_x$ group and the at least one (meth)acryloxy group are linked together by a C5-C12 hydrocarbon group; an ethylenically unsaturated compound without acid functionality; an initiator system; and a filler. Such compositions are described, for example, in U.S. Provisional Application Ser. No. 60/600,658 (Luchterhandt et al.), filed on Aug. 11, 2004.

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Epoxy (Oxirane) or Vinyl Ether Compounds

The hardenable compositions of the present invention may include one or more hardenable components in the form of epoxy (oxirane) compounds (which contain cationically active epoxy groups) or vinyl ether compounds (which contain cationically active vinyl ether groups), thereby forming hardenable compositions.

The epoxy or vinyl ether monomers can be used alone as the hardenable component in a dental composition or in combination with other monomer classes, e.g., ethylenically unsaturated compounds as described herein, and can include as part of their chemical structures aromatic groups, aliphatic groups, cycloaliphatic groups, and combinations thereof.

Examples of epoxy (oxirane) compounds include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, in some embodiments at least 1.5, and in other embodiments at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, carbosilane groups, nitro groups, phosphate groups, and the like. The molecular weight of the epoxy-containing materials may vary from 58 to 100,000 or more.

Suitable epoxy-containing materials useful as the resin system reactive components in the present invention are listed in U.S. Pat. No. 6,187,836 (Oxman et al.) and U.S. Pat. No. 6,084,004 (Weinmann et al.).

Other suitable epoxy resins useful as the resin system reactive components include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexyl-methyl) adipate. For a more detailed list of useful epoxides of this nature, reference is made to U.S. Pat. No. 6,245,828 (Weinmann et al.) and U.S. Pat. No. 5,037,861 (Crivello et al.); and U.S. Pat. Publication No. 2003/035899 (Klettke et al.).

Other epoxy resins that may be useful in the compositions of this invention include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262 (Schroeder), and in "Handbook of Epoxy Resins" by Lee and Neville, McGraw-Hill Book Co., New York (1967).

Other suitable epoxides useful as the resin system reactive components are those that contain silicon, useful examples of which are described in International Pat. Publication No. WO 01/51540 (Klettke et al.).

Additional suitable epoxides useful as the resin system reactive components include octadecylene oxide, epichlorohydrin, styrene oxide, vinyl cyclohexene oxide, glycidol, glycidylmethacrylate, diglycidyl ether of Bisphenol A and other commercially available epoxides, as provided in U.S. Ser. No. 10/719,598 (Oxman et al.; filed Nov. 21, 2003).

Blends of various epoxy-containing materials are also contemplated. Examples of such blends include two or more weight average molecular weight distributions of epoxy-containing compounds, such as low molecular weight (below 200), intermediate molecular weight (200 to 10,000) and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful hardenable components having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable components may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights (i.e., from 32 to 200), intermediate molecular weights (i.e., from 200 to 10,000, or high molecular weights (i.e., above 10,000). As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in the present invention are listed in U.S. Pat. No. 6,187,836 (Oxman et al.).

The hardenable component(s) may also contain hydroxyl groups and cationically active functional groups in a single molecule. An example is a single molecule that includes both hydroxyl groups and epoxy groups.

Glass Ionomers

The hardenable compositions of the present invention may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). RMGI cements are preferably formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

Polyethers or Polysiloxanes (ie., Silicones)

Dental impression materials are typically based on polyether or polysiloxane (i.e. silicone) chemistry. Polyether materials typically consist of a two-part system that includes a base component (e.g., a polyether with ethylene imine rings as terminal groups) and a catalyst (or accelerator) component (e.g., an aryl sulfonate as a cross-linking agent). Polysiloxane materials also typically consist of a two-part system that includes a base component (e.g., a polysiloxane, such as a dimethylpolysiloxane, of low to moderately low molecular weight) and a catalyst (or accelerator) component (e.g., a low to moderately low molecular weight polymer with vinyl terminal groups and chloroplatinic acid catalyst in the case of addition silicones; or a liquid that consists of stannous octanoate suspension and an alkyl silicate in the case of condensation silicones). Both systems also typically contain a filler, a plasticizer, a thickening agent, a coloring agent, or mixtures thereof. Exemplary polyether impression materials include those described in, for example, U.S. Pat. No. 6,127,449 (Bissinger et al.); U.S. Pat. No. 6,395,801 (Bissinger et al.); and U.S. Pat. No. 5,569,691 (Guggenberger et al.). Exemplary polysiloxane impression materials and related polysiloxane chemistry are described in, for example, U.S. Pat. No. 6,121,362 (Wanek et al.) and U.S. Pat. No. 6,566,413 Weinmann et al.), and EP Pat. Publication No. 1 475 069 A (Bissinger et al.).

Examples of commercial polyether and polysiloxane impression materials include, but are not limited to, IMPREGUM Polyether Materials, PERMADYNE Polyether Materials, EXPRESS Vinyl Polysiloxane Materials, DIMENSION Vinyl Polysiloxane Materials, and IMPRINT Vinyl Polysiloxane Materials; all available from 3M ESPE (St. Paul, Minn.). Other exemplary polyether, polysiloxane (silicones), and polysulfide impression materials are discussed in the following reference: Restorative Dental Materials, Tenth Edition, edited by Robert G. Craig and Marcus L. Ward, Mosby-Year Book, Inc., St. Louis, Mo., Chapter 11 (Impression Materials).

Photoinitiator Systems

In certain embodiments, the compositions of the present invention are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); in U.S. Pat. No. 5,856,373 (Kaisaki et al.), U.S. Pat. No. 6,084,004 (Weinmann et al.), U.S. Pat. No. 6,187,833 (Oxman et al.), and U.S. Pat. No. 6,187,836 (Oxman et al.); and in U.S. Pat. No. 6,765,036 (Dede et al.). The compositions of the invention can include one or more anthracene-based compounds as electron donors. In some embodiments, the compositions comprise multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Ser. No. 10/719,598 (Oxman et al.; filed Nov. 21, 2003).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroboarate. Suitable photosensitizers are monoketones and diketones that absorb some light within a range of 450 nm to 520 nm (preferably, 450 nm to 500 nm). More suitable compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino) benzoate and 2-butoxyethyl 4-(dimethylamino)benzoate; and polycondensed aromatic compounds (e.g. anthracene).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the composition. Preferably, the initiator system is present in a total amount of no more than 10 wt-%, more preferably, no more than 5 wt-%, and most preferably, no more than 2.5 wt-%, based on the weight of the composition.

Redox Initiator Systems

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements, resin-modified glass ionomer cements, redox cure systems, and combinations thereof.

The chemically hardenable compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the hardenable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the hardenable composition. Preferably, the reducing agent is present in an amount of no greater than 10% by weight, and more preferably no greater than 5% by weight, based on the total weight (including water) of the components of the hardenable composition.

Preferably, the oxidizing agent is present in an amount of at least 0.01% by weight, and more preferably at least 0.10% by weight, based on the total weight (including water) of the components of the hardenable composition. Preferably, the oxidizing agent is present in an amount of no greater than 10% by weight, and more preferably no greater than 5% by weight, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a hardenable composition such as described U.S. Pat. No. 5,154,762 (Mitra et al.).

Fillers

The compositions of the present invention can optionally contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 0.1 micrometers, and more preferably less than 0.075 micrometer.

The filler can be an inorganic material. It can also be a crosslinked organic material that is insoluble in the resin system (i.e., the hardenable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof Nanofillers are also described in U.S. patent application Ser. No. 10/847,781 (Kangas et al.); Ser. No. 10/847,782 (Kolb et al.); Ser. No. 10/847,803 (Craig et al.); and Ser. No. 10/847,805 (Budd et al.) all four of which were filed on May 17, 2004. These applications, in summary, describe the following nanofiller containing compositions.

U.S. patent application Ser. No. 10/847,781 (Kangas et al.) describes stable ionomer compositions (e.g., glass ionomer) containing nanofillers that provide the compositions with improved properties over previous ionomer compositions. In one embodiment, the composition is a hardenable dental composition comprising a polyacid (e.g., a polymer having a plurality of acidic repeating groups); an acid-reactive filler; at least 10 percent by weight nanofiller or a combination of nanofillers each having an average particle size no more than 200 nanometers; water; and optionally a polymerizable component (e.g., an ethylenically unsaturated compound, optionally with acid functionality).

U.S. patent application Ser. No. 10/847,782 (Kolb et al.) describes stable ionomer (e.g., glass ionomer) compositions containing nanozirconia fillers that provide the compositions with improved properties, such as ionomer systems that are optically translucent and radiopaque. The nanozirconia is surface modified with silanes to aid in the incorporation of the nanozirconia into ionomer compositions, which generally contain a polyacid that might otherwise interact with the nanozirconia causing coagulation or aggregation resulting in undesired visual opacity. In one aspect, the composition can be a hardenable dental composition including a polyacid; an acid-reactive filler; a nanozirconia filler having a plurality of silane-containing molecules attached onto the outer surface of the zirconia particles; water; and optionally a polymerizable component (e.g., an ethylenically unsaturated compound, optionally with acid functionality).

U.S. patent application Ser. No. 10/847,803 (Craig et al.) describes stable ionomer compositions (e.g., glass ionomers) containing nanofillers that provide the compositions with enhanced optical translucency. In one embodiment, the composition is a hardenable dental composition including a polyacid (e.g., a polymer having a plurality of acidic repeating groups); an acid-reactive filler; a nanofiller; an optional polymerizable component (e.g., an ethylenically unsaturated compound, optionally with acid functionality); and water. The refractive index of the combined mixture (measured in the hardened state or the unhardened state) of the polyacid, nanofiller, water and optional polymerizable component is generally within 4 percent of the refractive index of the acid-reactive filler, typically within 3 percent thereof, more typically within 1 percent thereof, and even more typically within 0.5 percent thereof.

U.S. patent application Ser. No. 10/847,805 (Budd et al.) describes dental compositions that can include an acid-reactive nanofiller (i.e., a nanostructured filler) and a hardenable resin (e.g., a polymerizable ethylenically unsaturated compound. The acid-reactive nanofiller can include an oxyfluoride material that is acid-reactive, non-fused, and includes a trivalent metal (e.g., alumina), oxygen, fluorine, an alkaline earth metal, and optionally silicon and/or a heavy metal.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., where the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition.

Optional Photobleachable and/or Thermochromic Dyes

In some embodiments, compositions of the present invention preferably have an initial color remarkably different than dental structures. Color is preferably imparted to the composition through the use of a photobleachable or photochromic dye. The composition preferably includes at least 0.001% by weight photobleachable or photochromic dye, and more preferably at least 0.002% by weight photobleachable or photochromic dye, based on the total weight of the composition. The composition preferably includes at most 1% by weight photobleachable or photochromic dye, and more preferably at most 0.1% by weight photobleachable or photochromic dye, based on the total weight of the composition. The amount of photobleachable and/or photochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Optional Thermallylabile Components

Optionally, the hardenable dental composition of the present invention can include a thermally labile component as described, for example, in U.S. patent application Ser. No. 11/275,246, filed the same day herewith entitled "DENTAL COMPOSITIONS INCLUDING A THERMALLY LABILE COMPONENT, AND THE USE THEREOF").

As used herein, a "thermally labile component" refers to a component (typically a compound) that includes one or more thermally labile groups. As used herein, a "thermally labile group" refers to a group that undergoes substantial breaking (e.g., observable by spectroscopic techniques) of chemical bonds within the group to form two or more separate groups upon heating to an elevated temperature (i.e., at least 42° C.). Preferably, the elevated temperature is no greater than 200° C., more preferably no greater than 150° C., and even more preferably no greater than 100° C., and most preferably no greater than 80° C. Suitable methods for determining whether substantial breaking of chemical bonds occurs upon heating a component to an elevated temperature would be apparent to one of skill in the art. Suitable methods include, for example, spectroscopic methods such as nuclear magnetic resonance (NMR) spectroscopy (including $^1$H, $^{13}$C, and/or other appropriate nuclei); and ultraviolet (UV), visible, and infrared (IR) spectroscopy, including near IR (NIR) spectroscopy. For example, $^1$H and/or $^{13}$C NMR spectra can be conveniently run in an NMR tube by dissolving the component in a solvent (e.g., CDCl$_3$), heating to an elevated temperature, and observing the disappearance of peaks arising from the component or the appearance of peaks arising from a reaction product at the desired temperature.

In certain embodiments, thermally labile components suitable for use in hardenable dental compositions of the present invention are preferably hardenable components that include one or more thermally labile groups. Typically, each thermally labile group is a multivalent group linking a plurality (i.e., two or more) of hardenable groups. In certain embodiments, the hardenable thermally labile component is an ethylenically unsaturated compound. For example, in such embodiments, the thermally labile group can be a divalent group linking two ethylenically unsaturated groups.

Thermally labile groups are well known in the art. Such groups include, for example, oxime esters as disclosed, for example, in U.S. Pat. No. 6,652,970 (Everaerts et al.), and groups including cycloaddition adducts as disclosed, for example, in U.S. Pat. No. 6,825,315 (Aubert), U.S. Pat. No. 6,147,141 (Iyer et al.), and PCT International Patent Application Publication No. WO 98/09913 (Rotello).

Optional Thermally Responsive Additives

Optionally, the hardenable dental composition of the present invention can include a thermally responsive additive as described, for example, in U.S. patent application Ser. No. 11/275,240, filed the same day herewith entitled "DENTAL COMPOSITIONS INCLUDING THERMALLY RESPONSIVE ADDITIVES, AND THE USE THEREOF").

As used herein, a "thermally responsive additive" is meant to include an additive that softens upon heating to a temperature (e.g., no greater than 200° C., preferably no greater than 150° C., more preferably no greater than 100° C., and most preferably no greater than 80° C.) that is below the decomposition temperature of the additive. Specifically, upon heating to an elevated temperature (i.e., at least 42° C.), the storage modulus of the additive at the elevated temperature decreases compared to the storage modulus of the additive at room temperature (e.g., 25° C.). Preferably, the storage modulus of the additive at the elevated temperature is at most 80%, more preferably at most 60%, 40%, 20%, 10%, 5%, 2%, 1%, 0.1%, or even 0.01 of the storage modulus of the additive at room temperature. Methods of measuring storage modulus of materials at specified temperatures are well known in the art and include those described, for example, in Rudin, "The Elements of Polymer Science and Engineering," 2$^{nd}$ Ed, Chapter 11, pp. (1999). Such methods include, for example, dynamic mechanical measurements by techniques such as dynamic mechanical analysis (DMA).

Such thermally responsive additives typically have a maximum in the rate of storage modulus decrease occurring typically within the range of 42° C. to 200° C. Such a maximum in the rate of storage modulus decrease can correspond to transitions including, for example, melt transitions ($T_m$), glass transitions ($T_g$), solid to smectic or nematic phase transitions in liquid crystals, isotropic melt transitions in liquid crystals, and the like.

In certain embodiments, softening of a hardened dental composition including a thermally responsive additive, upon heating to a temperature (e.g., no greater than 200° C., preferably no greater than 150° C., more preferably no greater than 100° C., and most preferably no greater than 80° C.) that is below the decomposition temperature of the additive, may optionally, but not necessarily, be observed to a greater extent than for the hardened dental composition not including a thermally responsive additive under similar conditions.

In some embodiments, thermally responsive additives can be polymers. Polymers having a wide variety of morphologies can be used. For example, a thermally responsive additive can be a semicrystalline polymer, an amorphous polymer, or a combination thereof. In some embodiments, thermally responsive additives can be liquid crystals (e.g., non-polymeric liquid crystals or polymeric liquid crystals). In some embodiments, thermally responsive additives can be waxes.

Useful semicrystalline polymers typically have a melt transition temperature ($T_m$) of at least 42° C. Useful semicrystalline polymers typically have a melt transition temperature ($T_m$) of at most 200° C., preferably at most 150° C., more preferably at most 100° C., and most preferably no greater than 80° C.

Useful amorphous polymers typically have a glass transition temperature ($T_g$) of at least 42° C. Useful amorphous polymers typically have a glass transition temperature ($T_g$) of at most 200° C., preferably at most 150° C., more preferably at most 100° C., and most preferably no greater than 80° C.

Examples of polymer classes that can be used for thermally responsive additives include poly((meth)acrylics), poly((meth)acrylamides), poly(alkenes), poly(dienes), poly(styrenes), poly(vinyl alcohol), poly(vinyl ketones), poly(vinyl esters), poly(vinyl ethers), poly(vinyl thioethers), poly(vinyl halides), poly(vinyl nitriles), poly(phenylenes), poly(anhydrides), poly(carbonates), poly(esters), poly(lactones), poly(ether ketones), poly(alkylene oxides), poly(urethanes), poly(siloxanes), poly(sulfides), poly(sulfones), poly(sulfonamides), poly(thioesters), poly(amides), poly(anilines), poly(imides), poly(imines), poly(ureas), poly(phosphazenes), poly(silanes), poly(silazanes), carbohydrates, gelatins, poly(acetals), poly(benzoxazoles), poly(carboranes), poly(oxadiazoles), poly(piperazines), poly(piperidines), poly(pyrazoles), poly(pyridines), poly(pyrrolidines), poly(triazines), and combinations thereof. One of skill in the art could select, without undue experimentation, polymers from the above-recited classes that have desired transition temperatures. See, for example, "Polymer Handbook," 4$^{th}$ Edition edited by J. Brandrup et al. (1999) for a list of melt transition temperatures and glass transition temperatures of selected polymers.

A wide variety of liquid crystals can be used for thermally responsive additives including, for example, those recited in "Liquid Crystals Handbook," volumes 1-3, edited by Demus et al. (1998). Suitable liquid crystals typically have an isotropic transition temperature of at least 42° C. Suitable liquid crystals typically have an isotropic transition temperature of at most 200° C., preferably at most 150° C., more preferably at most 100° C., and most preferably no greater than 80° C. One of skill in the art could select, without undue experimentation, liquid crystals that have desired transition temperatures.

Useful classes of liquid crystals include, for example, biphenyls (e.g., R-Ph-Ph-CN);

terphenyls (e.g., R-Ph-Ph-Ph-CN); esters (e.g., R-PhC(O)O-Ph-OR', R-PhC(O)O-Ph-CN, and R-PhC(O)O-Ph-Ph-CN); tolanes (e.g., R-Ph-C≡C-Ph-OR'); Schiff's bases (e.g., R-Ph-N═CH-Ph-OR' and R-O-Ph-CH═N-Ph-CN); azo compounds (R-Ph-N═N-Ph-OR'); azoxy compounds (e.g., R-Ph-N═N$^+$(O$^-$)-Ph-OR'); and stilbenes (e.g., R-Ph-C(Cl)═CH-Ph-OR'), where each R and R' independently represent an alkyl group. R is preferably a higher alkyl group, and typically at least a C7 alkyl group, and sometimes at least a C12 alkyl group. R' is preferably a lower alkyl group, and typically a C1 or C2 alkyl group.

Examples of waxes that can be used for thermally responsive additives include dental waxes such as pattern wax, baseplate wax, sheet wax, impression wax, study wax, polycaprolactone, polyvinylacetate, ethylene-vinyl acetate copolymer, polyethylene glycol, esters of carboxylic acids with long chain alcohols (e.g., behenyl acrylate), esters of long chain carboxylic acids with long chain alcohols (e.g., beeswax, a non-polymeric wax), petroleum waxes, oxidized polyethylene wax (e.g., a wax available under the trade designation CERIDUST 3719 from Clariant Corp., Charlotte, N.C.), micronized, polar, high density polyethylene wax (e.g., a wax available under the trade designation CERIDUST 3731 from Clariant Corp., Charlotte, N.C.), carnauba wax (e.g., a wax available under the trade designation MIWAX from Michelman Incorporated, Cincinnati, Ohio), and combinations thereof (e.g., blends including two or more of microcystalline waxes, carnauba wax, ceresin, and beeswax). Useful waxes can also be oligomeric or polymeric. Useful waxes can be macrocrystalline or microcrystalline, natural or synthetic, and they may contain functional groups (e.g., carboxyl, alcohol, ester, ketone, and/or amide groups). Suitable waxes melt at or above room temperature (e.g., 25° C.), and typically at or above 40° C., and sometimes at or above 50° C. Suitable waxes typically have low melt temperatures (e.g., no greater than 200° C., preferably no greater than 150° C., more preferably no greater than 100° C., even more preferably no greater than 90° C., and most preferably no greater than 80° C.). Suitable waxes can have a wide variety of physical properties. For example, at room temperature, physical properties of suitable waxes can range from kneadable to hard or brittle; coarse to crystalline; and/or transparent to opaque (with transparent being preferred).

Optional Radiation-to-Heat Converters

Optionally, the hardenable dental composition of the present invention can include a radiation-to-heat converter as described, for example, in U.S. patent application Ser. No. 11/275,243, filed the same day herewith entitled "DENTAL COMPOSITIONS INCLUDING RADIATION-TO-HEAT CONVERTERS, AND THE USE THEREOF"). Hardened dental compositions that include a radiation-to-heat converter can allow for heating the hardened dental composition by irradiating the composition.

A radiation-to-heat converter is typically a radiation absorber that absorbs incident radiation and converts at least a portion (e.g., at least 50%) of the incident radiation into heat. In some embodiments, the radiation-to-heat converter can absorb light in the infrared, visible, or ultraviolet regions of the electromagnetic spectrum and convert the absorbed radiation into heat. In other embodiments, the radiation-to-heat converter can absorb radio frequency (RF) radiation and convert the absorbed radiation into heat. The radiation absorber(s) are typically highly absorptive of the selected imaging radiation.

A wide variety of radiation-to-heat converters can be used including, for example, organic compounds, inorganic compounds, and metal-organic compounds. Such radiation-to-heat converters can include, for example, dyes (e.g., visible dyes, ultraviolet dyes, infrared dyes, fluorescent dyes, and radiation-polarizing dyes), pigments, metals, metal compounds, metal films, and other suitable absorbing materials. Many classes of organic and metal-organic dyes are described in "Infrared Absorbing Dyes", edited by Masaru Matsuoka, Plenum Press (New York, 1990). These classes of dyes include azo dyes, pyrazolone azo dyes, methine and cyanine dyes, porphyrin dyes, phthalocyanine dyes, quinine dyes such as anthraquinones and naphthaquinones, pyrylium and squarylium dyes, aminium and diimonium dyes. See, also, U.S. Pat. No. 6,759,177 (Shimada et al.). Radiation-to-heat converters can be selected as desired by one of skill in the art based on properties including, for example, solubility in and/or compatibility with the specific hardenable dental composition or solvent therefore, as well as the wavelength range of absorption. Typically, dyes and/or pigments are preferred for use as radiation-to-heat converters that absorb light in the infrared, visible, or ultraviolet regions of the electromagnetic spectrum.

For some embodiments, near infrared (NIR) absorbing pigments and/or dyes are preferred by use as radiation-to-heat converters to allow for heating by irradiating with NIR radiation. Such NIR absorbing materials typically absorb at wavelengths greater than 750 nanometers, and sometimes at wavelengths greater than 800, 850, or even 900 nanometers. Such NIR absorbing materials typically absorb at wavelengths less than 2000 nanometers, and sometimes at wavelengths less than 1500, 1200, or even 1000 nanometers.

A wide variety of pigments and/or dyes can be used as NIR absorbing radiation-to-heat converters. Useful pigments include, for example, indium tin oxide (ITO), antimony tin oxide (ATO), other tin oxide pigments, lanthanum hexaboride ($LAB_6$), porphyrin and phthalocyanine pigments, thioindigo pigments, carbon black, azo pigments, quinacridone pigments, nitroso pigments, natural pigments, and azine pigments. Useful dyes include, for example, NIR absorbing cyanine dyes, NIR absorbing azo dyes, NIR absorbing pyrazolone dyes, NIR absorbing phthalocyanine dyes, NIR absorbing anthraquinone and naphthaquinone dyes, nickel or platinum dithiolene complexes, squarilium dyes, carbonium dyes, methine dyes, diimonium dyes, aminium dyes, croconium dyes, quinoneimine dyes, and pyrylium dyes such as those available under the trade designations IR-27 and IR-140 from Sigma-Aldrich (St. Louis, Mo.) or Epolin Inc. (Newark, N.J.).

In some embodiments, the radiation-to-heat converter can be a radio frequency (RF) absorbing magnetic ceramic powder, to allow for heating by irradiating with RF radiation. Exemplary ceramic powders include, for example, NiZn ferrite available under the trade designation FERRITE N23 from National Magnetics Group (Bethlehem, Pa.) with a reported average particle size of 1.0 micrometer and a Curie Temperature ($T_c$) of 95° C.; and Mg—Mn—Zn mixed ferrite available under the trade designation FERRITE R from National Magnetics Group (Bethlehem, Pa.) with a reported average particle size of 1.0 micrometer and a Curie Temperature ($T_c$) of 90° C. Such ceramic powders are capable of absorbing radio frequency (RF) radiation and thereby increasing in temperature. At the reported Curie Temperatures, the ferrites will no longer absorb RF radiation and continue to increase in temperature. Typical RF radiation useful in this invention has an intensity range of 10 $\mu W/cm^2$ to 100 $\mu W/cm^2$ and a frequency of 10 KHz to 10 KHz.

Miscellaneous Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Pat. Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Methods

Hardenable and hardened dental compositions of the present invention (e.g., compositions that in certain embodiments include an acid-generating component and an acid-reactive component that includes one or more acid-reactive groups) can be used for a variety of dental and orthodontic applications that utilize a material capable of adhering (e.g., bonding) to a tooth structure. Preferred uses include applications in which it is desired that the hardened dental composition be removed from the tooth structure at some point in time. Uses for such hardenable and hardened dental compositions include, for example, uses as adhesives (e.g., dental and/or orthodontic adhesives), cements (e.g., glass ionomer cements, resin-modified glass ionomer cements, and orthodontic cements), primers (e.g., orthodontic primers), restoratives, liners, sealants (e.g., orthodontic sealants), coatings, and combinations thereof.

One preferred use for such hardenable or hardened dental compositions includes adhering an orthodontic appliance to a tooth structure. Exemplary embodiments for an orthodontic appliance having a hardenable or hardened dental composition of the present invention on the base thereof are illustrated in FIGS. 1-6. It should be noted that for such embodiments, a practitioner can apply the hardenable dental composition to the base of the orthodontic appliance, and then optionally harden the composition. Alternatively, an orthodontic appliance having a hardenable (or hardened) dental composition on the base thereof can be supplied, for example, by a manufacturer, as a "precoated" orthodontic appliance. In yet other embodiments, a practitioner can apply a hardenable dental composition (e.g., an orthodontic primer) to a tooth structure, optionally harden the composition, and then adhere the orthodontic appliance (typically having a hardenable orthodontic adhesive thereon) to the tooth structure.

Figure 2:
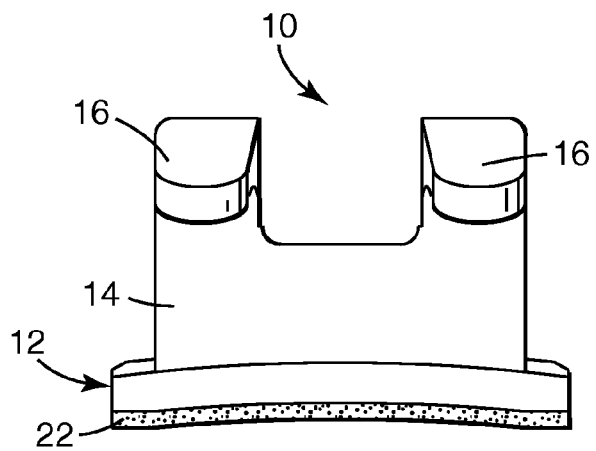
FIG. 2 is a side view of the orthodontic appliance of FIG. 1.

In FIGS. 1 and 2, an exemplary orthodontic appliance is designated by the numeral 10 and is a bracket, although other appliances such as buccal tubes, buttons and other attachments are also possible. The appliance 10 includes a base 12. The appliance 10 also has a body 14 that extends outwardly from the base 12. Base 12 can be a flange made of metal, plastic, ceramic, and combinations thereof. Base 12 can include a mesh-like structure, such as a fine wire screen. Base 12 can include particles (such as shards, grit, spheres, or other structure that optionally includes undercuts). Alternatively, the base 12 can be a custom base formed from one or more hardened dental composition layer(s) (e.g., hardened dental compositions of the present invention, hardened orthodontic adhesives, hardened orthodontic primers, or combinations thereof). Tiewings 16 are connected to the body 14, and an archwire slot 18 extends through a space between the tiewings 16. The base 12, the body 14, and tiewings 16 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, the base 12, the body 14, and the tiewings 16 are integrally made as a unitary component.

Figure 4:
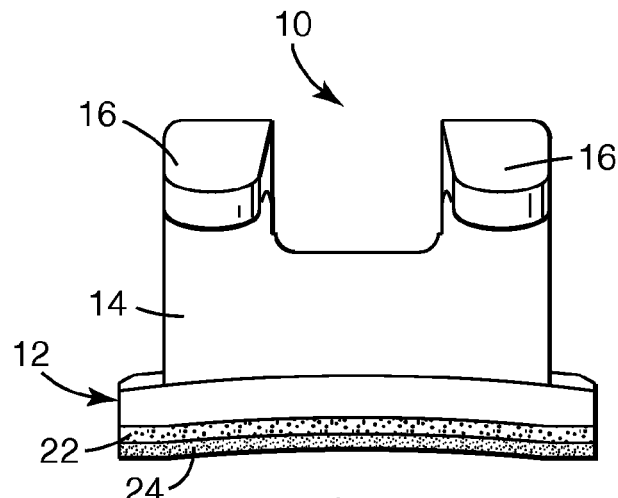
FIGS. 4-6 are side views of orthodontic appliances having a plurality of layers on the bases thereof, in which at least one layer of the plurality of layers is a hardenable or hardened dental composition of the present invention.
Figure 5:
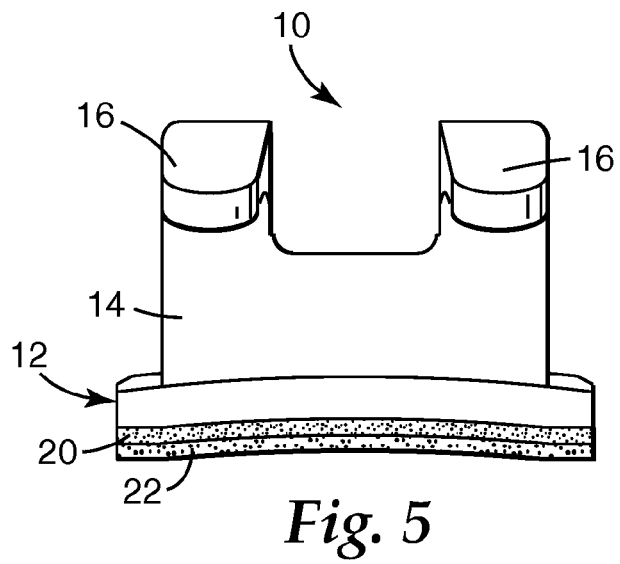
Figure 6:
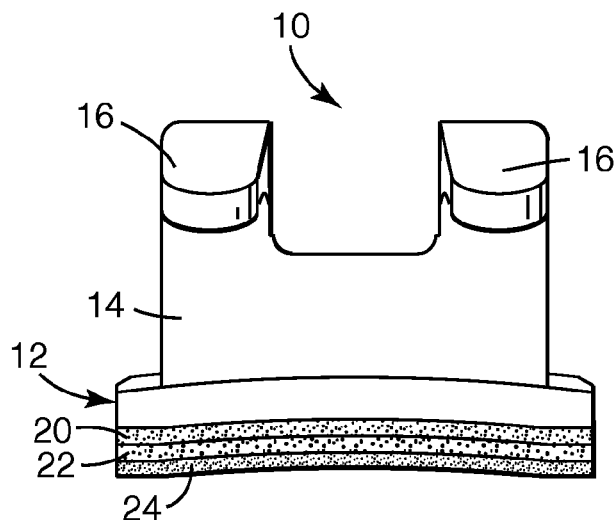

In the exemplary embodiment illustrated in FIGS. 1 and 2, a layer of a hardenable or hardened dental composition of the present invention 22 (hereinafter "composition layer 22"), which is typically an orthodontic adhesive, an orthodontic primer, or an orthodontic sealant, extends across the base 12 of the appliance 10. The composition layer 22 can serve in whole or at least in part to securely fix the appliance 10 to the patient's tooth by a bond having sufficient strength to resist unintended detachment from the tooth during the course of treatment. In one embodiment, the composition layer 22 is applied by the manufacturer to the base 12 of the appliance 10. It should be understood that orthodontic appliance 10 can optionally include additional layer(s) of dental compositions (e.g., orthodontic adhesives, orthodontic primers, or combinations thereof, which are not illustrated in FIGS. 1 and 2) in contact with composition layer 22. Specifically, such additional layer(s) can be between base 12 and composition layer 22; on composition layer 22 opposite base 12; or both. Such layers may or may not cover the same area, and may independently be discontinuous (e.g., a patterned layer) or continuous (e.g., non-patterned) materials extending across all or a portion of adhesive 22. Exemplary appliances including such additional layer(s) are illustrated in FIGS. 4-6.

Orthodontic appliances including multiple hardenable or hardened dental composition layers as described herein can be prepared by methods known to one of skill in the art. Suitable methods include, for example, applying, dispensing, or printing the layers of composition on an appliance or a substrate. Multiple layers may be applied simultaneously or sequentially.

A useful method for applying multiple layers of hardenable dental composition(s) on an orthodontic appliance or a substrate includes, for example, using automated fluid dispensing systems such as those available under the trade designation AUTOMOVE from Asymtek (Carlsbad, Calif.). Such automated fluid dispensing systems are useful for dispensing both patterned and non-patterned layers. Other useful systems include, for example, piston dispensing systems and multiple resolution fluid applicators as described, for example, in U.S. Pat. No. 6,513,897 (Tokie) and U.S. Pat. Application Publication No. 2005/0136370 A1 (Brennan et al.).

Once the hardenable dental composition layer(s) have been applied to an orthodontic appliance or a substrate, the appliance or substrate can conveniently be packaged in a container. Exemplary containers are well known in the art and are disclosed, for example, in U.S. Pat. No. 5,172,809 (Jacobs et al.) and U.S. Pat. No. 6,089,861 (Kelly et al.).

Figure 3:
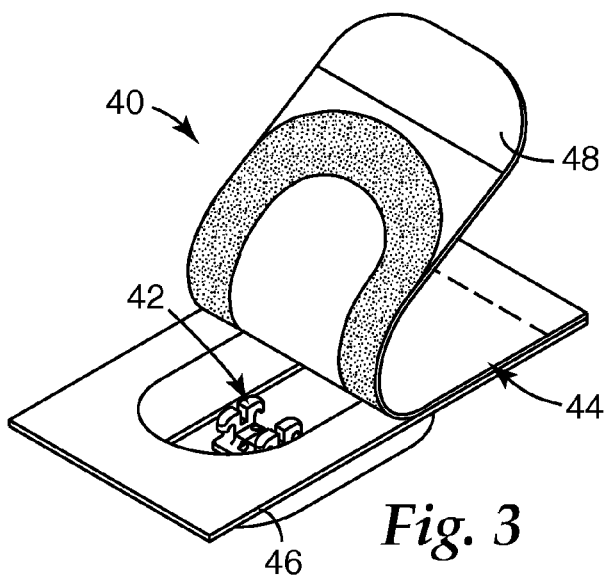
FIG. 3 is a perspective view of a packaged article illustrating an orthodontic appliance having a hardenable or hardened dental composition of the present invention on the base thereof in a container in which the cover has been partially opened.

Referring to FIG. 3, an exemplary embodiment of packaged article 40 including orthodontic appliance 42 having hardenable dental composition layer(s) coated on the base thereof is shown. Package 44 includes container 46 and cover 48. Cover 48, which is releasably connected to container 46 as initially provided, is peeled from container 46 to open the package for removal of orthodontic appliance 42. In FIG. 3, cover 48 has been peeled back from container 46 to partially open package 44.

In preferred embodiments, the package provides excellent protection against degradation of the hardenable dental composition(s) (e.g., photocurable materials), even after extended periods of time. Such containers are particularly useful for protecting dyes that impart a color changing feature to the adhesive. Such containers preferably effectively block the passage of actinic radiation over a broad spectral range, and as a result, the compositions do not prematurely lose color during storage.

In preferred embodiments, the package includes container 46 comprising a polymer and metallic particles. As an example, container 46 may be made of polypropylene that is compounded with aluminum filler or receives an aluminum powder coating as disclosed, for example, in U.S. Pat. Application Publication No. 2003/0196914 A1 (Tzou et al.). The combination of polymer and metallic particles provides a highly effective block to the passage of actinic radiation to color changing dyes, even though such dyes are known to be highly sensitive to light. Such containers also exhibit good vapor barrier properties. As a result, the rheological characteristics of the hardenable dental composition(s) are less likely to change over extended periods of time. For example, the improved vapor barrier properties of such containers provide substantial protection against degradation of the handling characteristics of adhesives so that the compositions do not prematurely cure or dry or become otherwise unsatisfactory. Suitable covers 48 for such containers can be made of any material that is substantially opaque to the transmission of actinic radiation so that the compositions do not prematurely cure. Examples of suitable materials for cover 48 include laminates of aluminum foil and polymers. For example, the laminate may comprise a layer of polyethyleneterephthalate, adhesive, aluminum foil, adhesive and oriented polypropylene.

In some embodiments, a packaged orthodontic appliance including a hardenable dental composition of the present invention thereon may include a release substrate as described, for example, in U.S. Pat. No. 6,183,249 (Brennan et al.).

In other embodiments, a packaged orthodontic appliance including a hardenable dental composition of the present invention thereon may not include a release substrate. In one embodiment, the package includes a substrate with at least one recess with an interior surface. The package includes a means for positioning the orthodontic appliance inside the recess such that the composition layer(s) do not separate from the appliance upon removal of the appliance from the recess. Preferably, the package further includes a cover for the recess and a means for maintaining the cover in contact with the substrate, wherein the means for positioning the orthodontic appliance includes means suspending the appliance in the recess such that the composition layer(s) do not contact the interior surface of the recess. Such packages are disclosed, for example, in U.S. Pat. No. 5,172,809 (Jacobs et al.).

In another embodiment the orthodontic appliance has a base for bonding the appliance to a tooth structure and a body extending from the base and at least two opposed tiewings extending away from the body. The base and at least one of the tiewings extend past the body in a gingival direction and present a gingival recess. The base and at least one other of the tiewings extend past the body in an occlusal direction and present an occlusal recess. The package includes a carrier having a pair of arms extending toward each other. Each of the arms has an outer end section, with the outer end sections being spaced apart from each other and presenting a channel therebetween. The orthodontic appliance is located in the channel and is supported by the arms with one of the outer end sections extending into the occlusal recess and the other of the outer end sections extending into the gingival recess. Such orthodontic appliances and packages are described, for example, in U.S. Pat. No. 6,089,861 (Kelly et al.).

In some embodiments, a packaged article can include a set of orthodontic appliances, wherein at least one of the appliances has a hardenable dental composition of the present invention thereon. Additional examples of articles and sets of appliances are described in U.S. Pat. Application Publication No. 2005/0133384 A1 (Cinader et al.). Packaged orthodontic appliances are described, for example, in U.S. Pat. Application Publication No. 2003/0196914 A1 (Tzou et al.) and U.S. Pat. No. 4,978,007 (Jacobs et al.), U.S. Pat. No. 5,015,180 (Randklev), U.S. Pat. No. 5,328,363 (Chester et al.), and U.S. Pat. No. 6,183,249 (Brennan et al.).

An orthodontic appliance having a hardenable dental composition of the present on the base thereof may be bonded to a tooth structure using methods (e.g., direct or indirect bonding methods) that are well known in the art. Upon application of the orthodontic appliance to the tooth structure, the hardenable dental composition of the present invention can be hardened to adhere the orthodontic appliance to the tooth structure. A variety of suitable methods of hardening the composition are known in the art. For example, in some embodiments the hardenable dental composition can be hardened by exposure to UV or visible light. In other embodiments, the hardenable dental composition can be provided as a multi-part composition that hardens upon combining the two or more parts.

When desired, typically upon completion of the orthodontic treatment process, the practitioner needs to remove the orthodontic appliance from the tooth structure. Hardened dental compositions of the present invention are designed to reduce the bond strength upon irradiating, and optionally heating, to allow for convenient removal of not only the orthodontic appliance, but also for removal of any hardened dental composition remaining on the tooth structure after removal of the appliance.

For embodiments in which the hardenable dental composition is photochemically hardened, the photochemical hardening and the irradiating (and optionally heating) to reduce the bond strength can be carried out using, for example, different wavelengths of radiation. For example, the acid-generator can be photosensitized at a desired wavelength of radiation as described, for example, in the Examples Section included herein.

The hardened dental composition can be heated by any convenient method including, but not limited to, heating with lasers, warm water, electrothermal debonding units, heated gel tray, as well as other methods known in the art.

Alternatively, for hardened dental compositions including radiation-to-heat converters, the hardened dental composition can optionally be heated by irradiation with radiation that is absorbed by the radiation-to-heat converter. A wide variety of radiation sources can be used including, for example, lasers, laser diodes, quartz-tungsten-halogen lamps, mercury lamps, doped mercury lamps, deuterium lamps, plasma arc lamps, LED sources, and other sources known in the art.

The hardened dental composition can optionally be heated to a convenient temperature for a time sufficient to decrease the bond strength and allow for convenient removal of the orthodontic appliance from the tooth structure. Preferably the temperature and time are chosen to prevent damage to the tooth structure as described, for example, in Zach et al. in "Endodontics," Bender, Editor, pp. 515-530 (1965). See, also, Laufer et al., Journal of Biomechanical Engineering, 107: 234-239 (1985); Launay et al., Lasers in Surgery and Medicine, 7:473-477(1987); Azzeh et al., American Journal of Orthodontics and Dentofacial Orthopedics, 123:79-83 (2003); and Uysal et al., Angle Orthodontist, 75:220-225 (2005). Typically, by using heating techniques that rapidly heat the dental composition, higher temperatures can be used for shorter durations without damaging the tooth structure.

In certain embodiments, at least a portion, and preferably all, of the hardened dental composition, optionally, is heated to at least 42° C., sometimes at least 50° C., and other times at least 70° C. Typically, the hardened dental composition is heated to at most 200° C., sometimes at most 150° C., other times to at most 100° C., and even other times to at most 80° C. The selected temperature is maintained for a time sufficient to result in the desired decrease in bond strength. In certain embodiments, the time is at most 10 minutes, sometimes at most 10 seconds, and other times at most 1 second. The decrease in bond strength typically results in fracture within the hardened composition layer.

In some embodiments, the orthodontic appliance includes an additional dental composition layer. Such additional dental composition layers can include, for example, unhardened or hardened dental compositions (e.g., in certain embodiments, a conventional dental composition not including an acid-generating component and an acid-reactive component). The inclusion of additional layers can influence, for example, where fracture takes place during debonding of the orthodontic appliance from the tooth structure, as described herein below.

For example, FIG. 4 illustrates an embodiment in which orthodontic appliance 10 has one additional dental composition layer 24 in contact with composition layer 22. Composition layer 22 may be either an unhardened or hardened dental composition of the present invention. Additional layer 24 is on composition layer 22 opposite base 12. Additional layer 24 is typically an unhardened dental composition (e.g., an orthodontic adhesive, an orthodontic primer, or a combination thereof). Upon application of orthodontic appliance 10 to a tooth structure, additional layer 24 (and composition layer 22 if not already hardened) can be hardened by a variety of methods as described herein above to adhere the orthodontic appliance to the tooth structure.

In some embodiments, additional layer 24 can be a hardenable orthodontic primer that is coated on the tooth structure (and optionally hardened) before the orthodontic appliance with composition layer 22 thereon is adhered to the tooth surface.

Upon completion of the orthodontic treatment, at least a portion of hardened composition layer 22 can be irradiated, and optionally heated, to reduce the bond strength, and preferably allow fracture within irradiated composition layer 22 upon removal of the orthodontic appliance. Fracture within irradiated composition layer 22 results in fracture near the orthodontic appliance and away from the tooth structure. Further, the irradiated, and optionally heated, hardened composition layer 22 (e.g., an orthodontic adhesive) typically has a lower modulus, and therefore is softer to allow for easier cleanup and/or removal of any remnants of the hardened composition. Therefore, after orthodontic treatment, one embodiment of FIG. 4 would be where composition layer 22 and additional layer 24 are both hardened orthodontic adhesives. In another embodiment, composition layer 22 would be a hardened orthodontic adhesive and additional layer 24 would be a hardened orthodontic primer.

FIG. 5 illustrates another embodiment in which orthodontic appliance 10 has one additional dental composition layer 20 in contact with composition layer 22. Additional layer 20 is between base 12 and composition layer 22. Additional layer 20 is typically an unhardened or hardened dental composition (e.g., an orthodontic adhesive, an orthodontic primer, or a combination thereof). Composition layer 22 is typically unhardened. Upon application of orthodontic appliance 10 to a tooth structure, composition layer 22 (and additional layer 20 if not already hardened) can be hardened by a variety of methods as described herein above to adhere the orthodontic appliance to the tooth structure.

In some embodiments, composition layer 22 can be a hardenable orthodontic primer that is coated on the tooth structure (and optionally hardened) before the orthodontic appliance with additional layer 20 thereon is adhered to the tooth surface.

Upon completion of the orthodontic treatment, at least a portion of hardened composition layer 22 can be irradiated, and optionally heated, to reduce the bond strength, and preferably allow fracture within irradiated composition layer 22 upon removal of the orthodontic appliance. Fracture within irradiated composition layer 22 results in fracture near the tooth structure. For embodiments in which composition layer 22 is an orthodontic primer and additional layer 20 is an orthodontic adhesive, the hardened orthodontic adhesive is substantially retained on the removed orthodontic appliance. As used herein, "substantially retained on the removed orthodontic appliance" means that at least 50% by weight, and preferably at least 75% by weight of the orthodontic adhesive is retained on the removed orthodontic appliance. When the hardened orthodontic adhesive is substantially retained on the removed orthodontic appliance, clean up and removal of any adhesive remaining on the tooth structure is more convenient, because less adhesive remains on the tooth structure. Additionally, any composition remaining on the tooth structure is preferably substantially the hardened dental composition of the present invention, which can optionally be heated to soften the composition, and thereby allow for easier adhesive removal. Therefore, after orthodontic treatment, one embodiment of FIG. 5 would be where composition layer 22 and additional layer 20 are both hardened orthodontic adhesives. In another embodiment, composition layer 22 would be a hardened orthodontic primer and additional layer 20 would be a hardened orthodontic adhesive.

For another example, FIG. 6 illustrates an embodiment in which orthodontic appliance 10 has two additional dental composition layers (20 and 24) in contact with composition layer 22. Additional layer 20 is between base 12 and composition layer 22. Additional layer 20 is typically an unhardened or hardened dental composition (e.g., an orthodontic adhesive, an orthodontic primer, or a combination thereof). Composition layer 22 can be unhardened or hardened. Additional layer 24 is on composition layer 22 opposite base 12. Additional layer 24 is typically an unhardened dental composition (e.g., an orthodontic adhesive, an orthodontic primer, or a combination thereof). Upon application of orthodontic appli ance 10 to a tooth structure, additional layer 24 (and composition layer 22 and additional layer 20, if not already hardened) can be hardened by a variety of methods as described herein above to adhere the orthodontic appliance to the tooth structure.

In some embodiments, additional layer 24 can be a hardenable orthodontic primer that is coated on the tooth structure (and optionally hardened) before the orthodontic appliance with additional layer 20 and composition layer 22 thereon is adhered to the tooth surface.

Upon completion of the orthodontic treatment, at least a portion of hardened composition layer 22 can be irradiated, and optionally heated, to reduce the bond strength, and preferably allow fracture within irradiated composition layer 22 upon removal of the orthodontic appliance. Fracture within irradiated composition layer 22 results in fracture between, yet safely away from, the orthodontic appliance and the tooth structure. Therefore, after orthodontic treatment, one embodiment of FIG. 6 would be where composition layer 22 and additional layers 20 and 24 are all hardened orthodontic adhesives. In another embodiment, composition layer 22 would be a hardened orthodontic adhesive and additional layers 20 and 24 would be hardened orthodontic primers.

It is to be understood that additional embodiments are contemplated in which additional layers or arrangements of layers are present. Further, the thickness of each layer can be individually varied as desired. Further, dental compositions of the present invention need not be present only in explicitly defined layers, but can also be present distributed uniformly or non-uniformly throughout all or a portion of the layer(s) present on the base of the orthodontic appliance.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Shear Bond Strength on Glass Test Method A

Orthodontic brackets were bonded to a glass slide surface by either thermal bonding or photo bonding procedures and then subjected to UVA or visible light irradiation for debonding as described in Examples 2-7. The light-irradiated bonded brackets (plus a non-irradiated bonded bracket control sample) were then sheared off of the glass slides using an Instron R5500 instrument (Instron Corp., Canton, Mass.) equipped with an oven equilibrated for 5 minutes at 100° C. and a 500-N load cell. Strain was applied at 0.5 cm/min and data were collected at 10 data points (dpts)/second. Data were reported in lb-f units and then converted to a force per unit area (MPa). Each experiment included at least four replications.

Therefore, the general procedure for debonding an adhered bracket from a surface was to irradiate the adhesive bond at about room temperature and then measure bond strength at about 100° C.

Shear Bond Strength on Glass Test Method B

Orthodontic brackets were bonded to a glass slide surface by a photobonding procedure and then subjected to UVA irradiation for debonding as described in Example 10. The UVA-irradiated bonded brackets (plus non-UVA-irradiated bonded brackets Control samples) were placed in a pre-equilibrated oven held for 100° C. for 5 minutes and allowed to cool to room temperature for 10 minutes. All brackets were then sheared off of the glass slides using an Instron R5500 instrument (Instron Corp., Canton, Mass.) equipped a 500-N load cell. Strain was applied at 0.5 cm/min and data were collected at 10 data points (dpts)/second. Data were reported in lb-f units and then converted to a force per unit area (MPa) and each experiment included six replications.

Shear Bond Strength on Glass Test Method C

Orthodontic brackets were bonded to a glass slide surface by a photobonding procedure and then subjected to UVA irradiation for debonding as described in Example 11. The UVA-irradiated bonded brackets (plus non-UVA-irradiated bonded brackets Control samples) were placed in a pre-equilibrated oven held for 70° C. for 3 minutes and allowed to cool to room temperature for 15 minutes. All brackets were then sheared off of the glass slides using an Instron R5500 instrument (Instron Corp., Canton, Mass.) equipped a 500-N load cell. Strain was applied at 0.5 cm/min and data were collected at 10 data points (dpts)/second. Data were reported in lb-f units and then converted to a force per unit area (MPa) and each experiment included ten replications.

Shear Bond Strength on Teeth Test Method A

Orthodontic brackets were bonded to bovine teeth surfaces by a photo bonding procedure and then about half the samples were subjected to UVA light irradiation for debonding as described in Example 8. For debonding, all the samples were subjected to a 20-second irradiation period with a modified Litema Astral light gun (Litema Dental, Baden-Baden, Germany) with its internal blue light metallized filter removed. During the irradiation period, the light gun was gently pressed against the top of the bonded bracket and the temperature of the adhesive layer (containing the near infrared (NIR) absorber TRB SH 7080) increased to about 100° C. Immediately after irradiation, the UVA light-irradiated bonded brackets (plus the non-UVA-irradiated bonded bracket control sample) were sheared off of the teeth surfaces using an Instron R5500 instrument (Instron Corp., Canton, Mass.) equipped with a 500-N load cell. Strain was applied at 0.5 cm/min and data were collected at 10 dpts/second. Data were reported in lb-f units and then converted to a force per unit area (MPa). Each experiment included at least six or seven replications.

Shear Bond Strength on Teeth Test Method

Orthodontic brackets were bonded to bovine teeth surfaces by a photobonding procedure and then about half the samples were subjected to UVA light irradiation for debonding as described in Example 12. For debonding, all the samples were subjected to a 20-second irradiation period with a modified Astral light gun (Litema Dental, Baden-Baden, Germany) with its internal blue light metallized filter removed. During the irradiation period, the light gun was gently pressed against the top of the bonded bracket and the temperature of the adhesive layer (containing the near infrared (NIR) absorber TRB SH 7080) increased to an estimated 100° C. Immediately after irradiation, the UVA light-irradiated bonded brackets (plus the non-UVA-irradiated bonded bracket control samples) were sheared off of the teeth surfaces using an Instron R5500 instrument (Instron Corp.) equipped with a 500-N load cell. Strain was applied at 0.5 cm/min and data were collected at 10 dpts/second. Data were reported in lb-f units and then converted to a force per unit area (MPa). Each experiment included four or five replications.

| Abbreviations, Descriptions, and Sources of Materials | |
|---|---|
| Abbreviation | Description and Source of Material |
| HEMA | 2-Hydroxyethyl methacrylate (Sigma-Aldrich, St. Louis, MO) |
| 2-EHA | 2-Ethylhexyl acrylate (Sigma-Aldrich) |
| t-BOCDMA | "Tertiary-butyloxycarbonyl 2-hydroxyethyl dimethacrylate" (See preparation method and chemical structure described herein.) |
| CHDVE | Cyclohexyl divinyl ether (1,4-bis(vinyloxymethyl)cyclohexane), (International Specialty Products, Wayne, NJ) |
| CHDVEDMA | Cyclohexyl divinyl ether dimethacrylate (1,4-bis(α-(methacryloyloxyethyloxymethyl)cyclohexane); see preparation method and chemical structure described herein. |
| $Ar_3S^+SbF_6^-$ | Triaryl sulfonium hexafluoroantimonate (Cyracure CPI-6976, Advanced Research Corporation, Catoosa, OK) |
| $Ar_3S^+PF_6^-$ | Triaryl sulfonium hexafluorophosphate, Cyracure CPI-6992, 50% solution in propylene carbonate (Aceto Corp., Lake Success, NY) |
| $Ar_3S^+N(SO_2CF_3)_2^-$ | Triaryl sulfonium N-(trifluoromethanesulfonyl)trifluoromethane-sulfonamido anion; prepared as generally described in U.S. Pat. No. 5,554,664 (Lamanna et al.); (Experimental Material No. L-15974, 3M Company, St. Paul, MN) |
| BPO | Benzoyl peroxide (Sigma-Aldrich) used as thermal initiator |
| IRGACURE 819 | Phosphine oxide photoinitiator (Ciba Specialty Chemicals Corp., Terrytown, NY) |
| 2-MA | 2-Methylanthracene photosensitizer (Sigma-Aldrich); purified by column chromatography with hexanes as the eluant |
| EDMOA | 2-Ethyl-9,10-dimethoxyanthracene photosensitizer (Sigma-Aldrich) |
| TRB SH 7080 | Blue-colored sol containing indium-tin-oxide (ITO) nanoparticles (40%; near infrared absorber) in methyl cellosolve (40%) and a urethane acrylate (20%) (Advanced NanoProducts, S. Korea) |
| SO-E2 Filler | Silica Powder; average particle size = 500 nm (Tatsumori Limited, Tokyo, Japan) |

Starting Material Preparatrions

Preparation of t-BOCDMA

Figure 7:
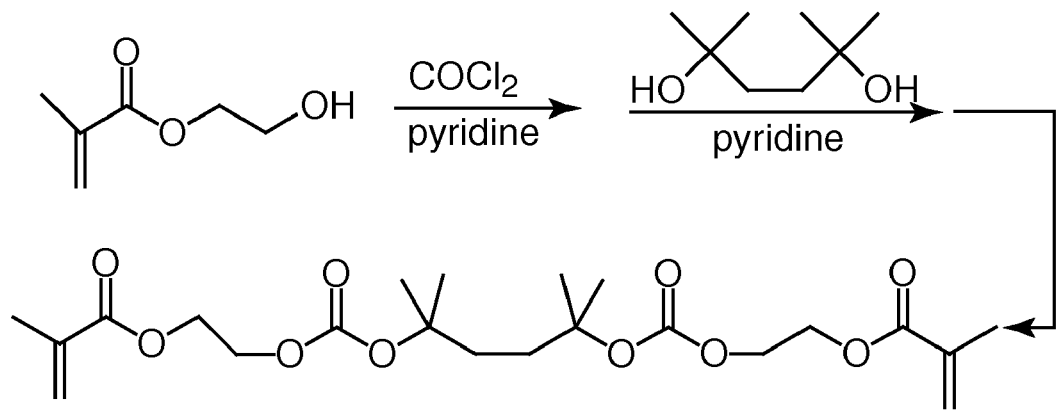
FIG. 7 is a schematic representation of an exemplary method for preparing tertiary-butyloxycarbonyl 2-hydroxyethyl dimethacrylate (t-BOCDMA) as described herein.

A schematic representation of an exemplary method for preparing t-BOCDMA is illustrated in FIG. 7. In brief, 2-(chloroformyl)ethyl methacrylate, either isolated or prepared in situ, is allowed to react with 2,5-dimethylhexane-2,5-diol as described herein below.

Synthesis and isolation of 2-(chloroformyl)ethyl methacrylate. A solution of HEMA (7.24 g) and dry pyridine (6.5 ml, distilled from calcium hydride) was prepared in dry toluene (50 ml, J T Baker) by stirring under nitrogen in an ice bath. To this solution was added dropwise a solution of phosgene in toluene (36 ml, Sigma-Aldrich) with stirring. A colorless precipitate formed immediately. The mixture was stirred for two hours and vacuum filtered in a fume hood to yield a colorless filtrate. The filtrate was evaporated to dryness using a rotary evaporator in a fume hood to yield a pale yellow oil. The oil was further dried using a vacuum pump (<5 Torr). The yield was 6.35 g and the structure was determined by proton NMR to be 2-(chloroformyl)ethyl methacrylate.

Synthesis and purification of the mono methacrylate ester (Compound A) derived from the reaction of 2-(chloroformyl) ethyl methacrylate (prepared in situ from triphosgene and HEMA) and 2,5-dimethylhexane-2,5-diol. A solution of triphosgene (3.91, Sigma-Aldrich) in methylene chloride (150 ml, J T Baker) was prepared under nitrogen in an ice bath with stirring. Dry pyridine (3.2 ml, distilled from calcium hydride) was added dropwise to the solution with stirring. An exothermic reaction occurred and the solution turned yellow with some precipitation. After stirring for 30 minutes the solution turned clear yellow. The solution was cooled in an ice bath and HEMA (5.11 g) in methylene chloride (10 ml) was added dropwise. After stirring for 30 minutes, another 3.2 ml of dry pyridine was added dropwise immediately followed by the addition of 2,5-dimethylhexane-2,5-diol (2.87 g, Sigma-Aldrich). The resultant pale yellow solution was stirred for 30 minutes followed by stripping of the solvent using a rotary evaporator. The resultant pasty yellow mixture was stirred in toluene (100 ml) for 1 hour in air and vacuum filtered. Rotary evaporation yielded a yellow oil that was purified by liquid chromatography ($SiO_2$, hexanes:ethyl acetate 10 to 35% gradient) to yield Compound A (3.05 g). The structure of Compound A was determined by proton NMR to be the 2-hydroxy 5-mono(methacrylate ester) reaction product of 2-(chloroformyl)ethyl methacrylate and 2,5-dimethylhexane-2,5-diol.

Synthesis and purification of t-BOCDMA. A solution of Compound A (4.60 g) and dry pyridine (1.7 ml, distilled from calcium hydride) was prepared in dry toluene (50 ml, J T Baker) by stirring under nitrogen in an ice bath. 2-(Chloroformyl)ethyl methacrylate (3.25 g) was added dropwise to the solution with stirring. The resultant mixture was vacuum filtered after 2 hours using CELITE as a filter aid. The filtrate was rotary evaporated to yield a nearly colorless oil that was stabilized with 30 ppm of tris(N-nitroso-N-isopropylhydroxylaminato)aluminum (NPAL, Albemarle, Baton Rouge, La.). The oil was purified by repeated liquid chromatography ($SiO_2$, hexanes:ethyl acetate 10 to 35% gradient followed by $SiO_2$ with methylene chloride:methanol 0 to 5% gradient). The yield of t-BOCDMA was 1.35 g. The structure of t-BOCDMA (shown above) was determined by proton NMR to be the 2,5-bis(methacrylate ester) reaction product of 2-(chloroformyl)ethyl methacrylate and Compound A.

Preparation of CHDVEDMA

Figure 8:
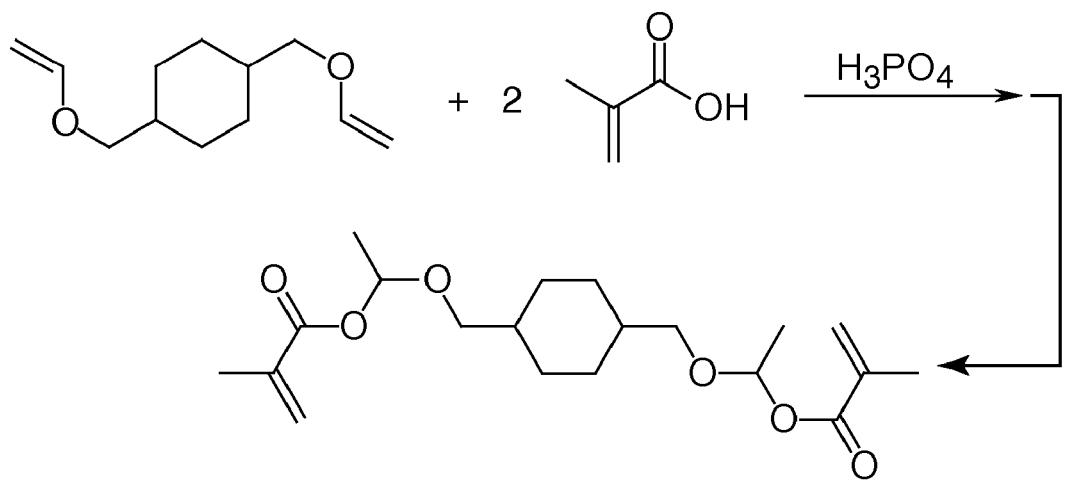
FIG. 8 is a schematic representation of an exemplary method for preparing cyclohexyl divinyl ether dimethacrylate (CHDVEDMA) as described herein.

A schematic representation of an exemplary method for preparing CHDVEDMA is illustrated in FIG. 8. In brief, cyclohexyl divinyl ether is allowed to react with methacrylic acid as described herein below.

Synthesis and purification of CHDVEDMA. A mixture of methacrylic acid (12.17 g, Sigma-Aldrich) and CHDVE (25.00 g) was prepared in a 250-ml round bottom flask equipped with a magnetic stirrer and an ice bath. A drop of phosphoric acid (J T Baker) was added to the mixture and the mixture stirred for 3 hours and allowed to attain room temperature spontaneously. After 3 hours of stirring, an additional 10.89 gm of methacrylic acid was added. The resulting mixture was stirred overnight under nitrogen. Finely ground anhydrous potassium carbonate (10.09 g, J T Baker) was then added and the resulting mixture stirred for 2 hours at room temperature. A thick, colorless suspension resulted that was taken up in anhydrous ethyl acetate (J T Baker) and filtered through a CELITE filter pad and subsequently through a 4-8 µm porosity glass frit (Ace Glass) to yield a colorless solution with a slight haze to it. Tris(N-nitroso-N-phenyl hydroxylamine) aluminum (4.8 mg, Albemarle, Baton Rouge, La.) was added to the solution and the solvent removed on a rotary evaporator at less than 10° C. A colorless oil was recovered with a yield of 41.1 gm. The structure of CHDVEDMA (shown above) was confirmed by proton NMR.

Example 1

Thermogravimetry Evaluation of t-BOCDMA/2-EHA Films

In order to demonstrate the photosensitivity property of t-BOCDMA, a film containing t-BOCDMA was prepared and subjected to thermogravimetry according to the following procedures.

A polymeric network (film) consisting of 6.4% t-BOCDMA and 1.9% $Ar_3S^+$ $SbF_6^-$ in 2-EHA (57.4%) was prepared thermally as follows using 0.7% lauroyl peroxide (Sigma-Aldrich) with propylene carbonate (33.6%) as a solvent. The composition was poured into a mold prepared by adhering 2 layers of VHB tape (3M Company) to a 2-mil thick polyester release liner that had been silicone treated on both sides. Another strip of the same release liner was used to cover the mold. The entire assembly was placed in an oven that was heated from room temperature to 90° C. over 20 minutes, held at 90° C. for 30 minutes followed by a cool down to 40° C. over 20 minutes. After curing, the sample was removed from the mold by peeling away the release liner and pushing out the polymer. The cured polymer strips were approximately 2.5 mm×2.5 mm and 0.23-mm thick.

Samples of the film (1.6 to 4.7 mg, 0.23-mm thickness) were irradiated with a Lesco SuperSpot Max UV-Curing System (Lesco, Torrance, Calif.) for varying durations of time (0.1 second, 0.2 seconds, 0.5 seconds, 1.0 second and 2.0 seconds) and then tested using thermogravimetry (TGA).

TGA results showed a distinct loss of mass on heating (ramp rate was 10° C./min) after a 50 mJ/$cm^2$ exposure. Initially, as temperature was increased to about 70° C. there was some loss of weight due to propylene carbonate evaporation from the thin film in the irradiated sample as well as the non-irradiated control. Thereafter, at temperatures between 70° C. to 150° C. there was loss of mass from the irradiated sample (that presumably corresponded to the loss of $CO_2$, an alkene, and oligomeric fragments after network degradation) but little or no loss of mass from the unirradiated control sample. These data suggest that a very low UVA (315 to 400 nm radiation) dose is required to generate enough photoacid (i.e., defined as protons generated by irradiation) to cause, after heating, cleavage of the t-BOC (tertiary-butyl carbonyl) group.

Example 2

Thermal Bonding and Photothermal Debonding on Glass Using an Adhesive Containing t-BOCDMA/HEMA/BPO/Sulfonium Salt In order to demonstrate the thermal bonding (i.e., bonding after exposure to heat) and photothermal debonding (i.e., debonding after sequential exposure to irradiation and then heat) properties of adhesives containing t-BOCDMA, an adhesive coating containing t-BOCDMA was prepared and thermally cured to adhere an orthodontic bracket to a glass slide. The adhered bracket was subjected to sequential UVA irradiation and heat, and shear bond strengths determined. These procedures were carried out according to the following details.

An adhesive formulation (Example 2) containing HEMA (86.5%), t-BOCDMA (10.0%), $Ar_3S^+$ $SbF_6^-$ (2.6%) and BPO (0.9%) was prepared. Window glass slides (3-mm thickness) were cleaned with methanol just prior to use. Approximately 10 mg of the formulation was placed on the non-fluorescent side of the cleaned slide as a single drop. A TRANSCEND 6000 ceramic bracket (Part Nos. 59543-01 and 59543-02, 3M Unitek, Monrovia, Calif.) was placed into the drop of adhesive formulation and thermally cured at 90° C. for 15 minutes on a programmable hotplate. The slide was allowed to cool to ambient temperature (about 23° C.) on the hotplate. Five replications were prepared for each experiment.

For the debonding experiments, the bonded bracket samples were irradiated by exposure to UVA at room temperature using a medium pressure Hg spot cure lamp (100 W, Super Spot Max, Lesco, Torrance, Calif.) fitted with a 300-nm filter. Light intensities were measured using an EIT Powerpuck (EIT, Inc. Sterling, Va.) and were measured to be in the 0.25 W/cm² to 0.35 W/cm² range. Irradiation was for 0 (Control), 1, 2, and 4 seconds to vary the irradiation dose and was performed through the glass slide. Bond strengths were then determined at 100° C. according to the Shear Bond Strength on Glass Test Method A described herein. Results are shown in Table 1 for 5 Runs at each of the different levels of irradiation plus an average result for each level.

TABLE 1

Debonding of Ceramic Brackets from Glass Surface.
Shear Data (MPa) at 100° C.

| Run | No UV | 1 sec UV | 2 sec UV | 4 sec UV |
|---|---|---|---|---|
| 1 | 3.20 | 3.04 | 2.01 | 1.07 |
| 2 | 2.95 | 3.37 | 1.93 | 1.37 |
| 3 | 3.63 | 3.56 | 1.99 | 1.62 |
| 4 | 3.69 | 3.21 | 1.91 | 0.82 |
| 5 | 2.52 | 2.47 | 2.52 | 1.57 |
| Average: | 3.20 | 3.13 | 2.07 | 1.29 |

It is seen from the data in Table 1 that increased irradiation of the bonded brackets resulted in decreased bond strength at 100° C. There was greater than 50% loss in adhesion for the Run Average at 4 seconds UV exposure (1.29 MPa) relative to the non-irradiated control (3.20 MPa). Significantly, the Instron data (when plotted as displacement vs. the shear loading) showed a sharp failure of the adhesive bonds in the non-irradiated samples whereas the adhesive bonds of the irradiated samples behaved more as a thermoplastic material that undergoes creep.

Example 3

Photobonding and Photothermal Debonding on Glass Using an Adhesive Containing t-BOCDMA/HEMA/IRGACURE/Sulfonium Salt In order to demonstrate the photobonding (i.e., bonding after exposure to radiation) and photothermal debonding properties of adhesives containing t-BOCDMA, an adhesive coating containing t-BOCDMA was prepared and photochemically cured to adhere an orthodontic bracket to a glass slide. The adhered bracket was subjected to sequential UVA irradiation and heat, and shear bond strengths determined. These procedures were carried out as follows.

An adhesive formulation (Example 3) consisting of HEMA (86.8%), t-BOCDMA (9.6%), $Ar_3S^+$ $PF_6^-$ (2.6%, 50% solution in propylene carbonate) and IRGACURE 819 (0.9%) was prepared. The procedure for preparing the glass slides was identical to that described in Example 2. Approximately 10 mg of the formulation was placed on the non-fluorescent side of the cleaned slide as a single drop. A TRANSCEND 6000 ceramic bracket (Part Nos. 59543-01 and 59543-02, 3M Unitek) was placed into the drop of adhesive formulation and bonding was carried out by irradiation through the glass slide using the Lesco light source through a narrow-band 440-nm interference filter (Esco Products, Oak Ridge, N.J.) for 50 seconds. Four replications were prepared for each experiment.

For the debonding experiments, the filter was removed from the Lesco light source and the bonded bracket samples were irradiated for 30 seconds through the glass slide. A non-irradiated bonded bracket sample served as a Control sample. Bond strengths were then determined at 100° C. according to the Shear Bond Strength on Glass Test Method A described herein. Results are shown in Table 2 for 4 Runs at the two different levels of irradiation (30 seconds and 0 seconds) plus an average result for each level.

TABLE 2

Debonding of Ceramic Brackets from Glass Surface.
Shear Data (MPa) at 100° C.

| Run | No UV | 30 sec UV |
|---|---|---|
| 1 | 3.40 | 0.13 |
| 2 | 4.35 | 0.03 |
| 3 | 3.86 | 0.06 |
| 4 | 6.84 | 0.09 |
| Average: | 4.61 | 0.08 |

It is seen from the data in Table 2 that there is a significant failure at 100° C. in adhesion of the irradiated (during debonding) bracket sample relative to the non-irradiated control sample.

Examples 2 and 3 demonstrate that the use of adhesive coatings containing t-BOCDMA permit the debonding of orthodontic brackets from glass surfaces with a high degree of efficiency.

Example 4

Photobonding and Photothermal Debonding on Glass Using an Adhesive Containing t-BOCDMA/HEMA/IRGACURE/Sulfonium Salt/Photosensitizer In order to demonstrate the photobonding and photothermal debonding properties of adhesives containing t-BOCDMA, an adhesive coating containing t-BOCDMA was prepared and photochemically cured to adhere an orthodontic bracket to a glass slide. The adhered bracket was subjected to sequential visible light irradiation and heat, and shear bond strengths determined. These procedures were carried out as follows.

An adhesive formulation (Example 4) consisting of HEMA (85.9%), t-BOCDMA (9.9%), $Ar_3S^+ N(SO_2CF_3)_2^-$ (2.6%), IRGACURE 819 (0.8%), and 2-MA (0.4%) was prepared. A small quantity of methylene chloride was used to dissolve the 2-MA, and the methylene chloride was subsequently removed from the formulation using a stream of dry nitrogen gas followed by vacuum evaporation a 3 Torr for 5 minutes. This formulation was used to bond Transcend 6000 ceramic brackets (Part No. 59543-01, 3M Unitek) to cleaned window glass slides as described in Example 3. It was estimated that the light intensity was 120 mW/cm². Five replications were prepared for each experiment.

For the debonding experiments, the bonded bracket samples were irradiated through the glass slide by exposure to visible light at room temperature for 50 seconds using the same LESCO Super Spot Max light source (see Example 2), but fitted with a long pass GG385 filter (Esco Products). The GG385 filter transmits light at longer than 385 nm resulting in irradiation and activation of the 2-MA. The 2-MA acts as a photosensitizer for the $Ar_3S^+ N(SO_2CF_3)_2^-$ causing the generation of photoacid that reacts with the acid-reactive functionality in the cross-linked polymer backbone. A non-irradiated bonded bracket sample served as a Control sample. Bond strengths were then determined at 100° C. according to the Shear Bond Strength on Glass Test Method A described herein. Results are shown in Table 3 for 5 Runs at the two different levels of irradiation (50 seconds and 0 seconds) plus an average result for each level.

TABLE 3

Debonding of Ceramic Brackets from Glass Surface. Shear Data (MPa) at 100° C.

| Run | No Visible Light | 50 sec Visible Light |
|---|---|---|
| 1 | 2.97 | 1.12 |
| 2 | 2.89 | 1.26 |
| 3 | 3.72 | 0.71 |
| 4 | 2.48 | 1.45 |
| 5 | 2.71 | 1.11 |
| Average: | 2.95 | 1.13 |

It is seen from the data in Table 3 that there is a significant failure at 100° C. in adhesion of the bracket sample irradiated with visible light (during debonding) relative to the non-irradiated control sample. It is noted that the control bond strength was somewhat lower than typical bond strengths for this assembly, most likely due to the incomplete removal of methylene chloride (which can act as a chain transfer agent) from the adhesive formulation and from the higher temperature. Room temperature results are generally in the 7-10 MPa region for related adhesive formulations.

Example 5

Photobonding and Photothermal Debonding on Glass Using an Adhesive Containing t-BOCDMA/HEMA/IRGACURE/Sulfonium Salt/Photosensitizer An adhesive formulation was prepared as described for Example 4, except that heat was used to dissolve the 2-MA in the HEMA prior to the addition of the other components, and no methylene chloride solvent was used. The heat was provided from a heat gun held about 3 cm from the vial containing the 2 ingredients and applied with gentle shaking of the vial until the 2-MA dissolved in the HEMA. The photobonding and photothermal debonding procedures were the same as described for Example 4, except that the ceramic bracket samples were irradiated for 100 seconds instead of 50 seconds for the debonding procedure. Bond strengths were then determined at 100° C. according to the Shear Bond Strength on Glass Test Method A described herein. Five replications were prepared for each experiment.

Results are shown in Table 4 for 5 Runs at the two different levels of irradiation (100 seconds and 0 seconds) plus an average result for each level.

TABLE 4

Debonding of Ceramic Brackets from Glass Surface. Shear Data (MPa) at 100° C.

| Run | No Visible Light | 100 sec Visible Light |
|---|---|---|
| 1 | 5.67 | 0.99 |
| 2 | 3.36 | 0.96 |
| 3 | 3.75 | 2.74 |
| 4 | 4.64 | 1.69 |
| 5 | 3.63 | 1.87 |
| Average: | 4.21 | 1.65 |

It is seen from the data in Table 4 that the bracket sample irradiated with visible light (during debonding) had again a significantly smaller bond strength relative to the non-irradiated control sample. The bond strength of the irradiated sample was slightly higher than observed in Example 4, a result attributed to the possible secondary crosslinking that could occur during the longer (100 vs. 50 seconds) irradiation period. It is noted that the Control bond strength was higher than in Example 4 and more typical of bond strengths for this assembly.

Example 6

Photobonding and Photothermal Debonding on Glass Using an Adhesive Containing t-BOCDMA/HEMA/IRGACURE/Sulfonium Salt/Photosensitizer An adhesive formulation was prepared as described for Example 5 with heat used to dissolve the 2-MA in the HEMA prior to the addition of the other components, and no methylene chloride solvent was used. The photobonding and photothermal debonding procedures were the same as described for Example 4 with the bracket samples irradiated for 50 seconds for both procedures. Bond strengths were then determined at 100° C. according to the Shear Bond Strength on Glass Test Method A described herein. Five replications were prepared for each experiment.

Results are shown in Table 5 for 5 Runs at the two different levels of irradiation (50 seconds and 0 seconds) plus an average result for each level.

TABLE 5

Debonding of Ceramic Brackets from Glass Surface.
Shear Data (MPa) at 100° C.

| Run | No Visible Light | 50 sec Visible Light |
|---|---|---|
| 1 | 2.97 | 1.23 |
| 2 | 4.31 | 0.97 |
| 3 | 4.11 | 1.02 |
| 4 | 3.37 | 0.98 |
| 5 | 4.22 | 0.73 |
| Average: | 3.80 | 0.99 |

Once again, as is seen from the data in Table 5, the bracket sample irradiated with visible light (during debonding) had a significantly lower bond strength relative to the non-irradiated Control sample.

Example 7

Photobonding and Photothermal Debonding on Glass Using an Adhesive Containing t-BOCDMA/HEMA/IRGACURE/Sulfonium Salt/Photosensitizer An adhesive formulation (Example 7) was prepared as described for Example 6, except that EDMOA photosensitizer was used in place of 2-MA. The photobonding and photothermal debonding procedures were the same as described for Example 4 with the ceramic bracket samples irradiated for 50 seconds with the Lesco light source (with 440-nm filter) for the bonding procedure; and for 50 seconds (or no irradiation for the Control sample) with the Lesco light source (with long pass GG385 filter) during the debonding procedure. Bond strengths were then determined at 100° C. according to the Shear Bond Strength on Glass Test Method A described herein. Five replications were prepared for each experiment.

Results are shown in Table 6 for 5 Runs at the two different levels of irradiation (50 seconds and 0 seconds) plus an average result for each level.

TABLE 6

Debonding of Ceramic Brackets from Glass Surface.
Shear Data (MPa) at 100° C.

| Run | No UV | 50 sec UV |
|---|---|---|
| 1 | 0.86 | 0.76 |
| 2 | 1.02 | 0.96 |
| 3 | 0.77 | 1.18 |
| 4 | 0.94 | 1.06 |
| 5 | 0.94 | 0.88 |
| Average: | 0.91 | 0.97 |

It is seen from the data in Table 6 that the bond strengths were low for the irradiated (during debonding) bonded bracket sample and also for the non-irradiated Control bonded bracket sample, and that there was no significant bond strength difference between the two samples. These results are attributed to a possible competitive absorption between the EDMOA photosensitizer ($\lambda_{max}$ about 430 nm) and the IRGACURE photoinitiator (430-440 nm photobonding wavelength range), such that there was likely a premature activation (i.e., premature generation of photoacid) of all the bracket samples during the bonding irradiation procedure; and subsequent loss of bond strength for both the irradiated (during debonding) and non-irradiated control bracket samples during the heating (at 100° C.) step of the debonding procedure.

Example 8

Photobonding and Photothermal Debonding on Teeth Using an Adhesive Containing t-BOCDMA/HEMA/IRGACURE/Sulfonium Salt/NIR-Absorber In order to demonstrate the photobonding and photothermal debonding properties of adhesives containing t-BOCDMA, an adhesive coating containing t-BOCDMA was prepared and photochemically cured to adhere orthodontic brackets to bovine teeth surfaces. The adhered brackets were subjected to sequential UVA light irradiation and heat (generated by white-light irradiation of the near infrared (NIR)-absorber present in the adhesive), and shear bond strengths determined. These procedures were carried out as follows.

An adhesive formulation (Example 8) consisting of HEMA (51.1%), t-BOCDMA (5.7%), $Ar_3S^+$ $PF_6^-$ (5.4% of a 50% solution in propylene carbonate), IRGACURE 819 (0.5%), TRB SH 7080 NIR-absorber (2.1%), and SO-E2 silica powder filler (35.2%) was prepared by mixing the components in a Branson Model 2510 ultrasonic bath (Branson, Danbury, Conn.) for 20 minutes.

Thirteen bovine teeth were potted in a poly(methyl methacrylate) base and were etched and primed using ADPER PROMPT L-Pop self-etching adhesive (3M ESPE, St. Paul, Minn.) for 30 seconds followed by blowing with a stream of air to remove excess adhesive. Approximately 10 mg (one drop) of the adhesive formulation was placed on a treated tooth surface. A TRANSCEND 6000 ceramic bracket (Part Nos. 59543-01, 3M Unitek) was carefully placed into the drop of adhesive formulation and bonding was carried out by irradiating all 13 bracket samples with a Lesco Super Spot Max light source fitted with a 420-nm long pass filter (GG 420, Esco Products). Irradiation was carried out three times for 15 seconds with 30-second intervals.

For the debonding experiments, six of the bonded bracket samples (Controls) were irradiated by exposure for 6 cycles of 10 seconds each with 30-second intervals to the same LESCO Super Spot Max light source (fitted with the 420-nm long pass GG 420 filter; thus, to mimic the heat provided from the light source, but without UVA light). Seven of the bonded bracket samples were irradiated by exposure for 6 cycles of 10 seconds each with 30-second intervals to UVA light using the same LESCO Super Spot Max light source (but without the filter). Bond strengths were then determined at about 100° C. according to the Shear Bond Strength on Teeth Test Method A described herein.

Results are shown in Table 7 for 6 Runs with no UV irradiation and 7 Runs with 60 seconds of UV irradiation plus an average result for each series of Runs.

TABLE 7

Debonding of Ceramic Brackets from Glass Surface.
Shear Data (MPa) at 100° C.

| Run | No UV | 60 sec UV |
| --- | --- | --- |
| 1 | 4.78 | 1.09 |
| 2 | 5.24 | 0.62 |
| 3 | 3.77 | 0.78 |
| 4 | 9.09 | 0.98 |
| 5 | 8.67 | 1.37 |
| 6 | 3.29 | 1.13 |
| 7 | — | 1.11 |
| Average: | 5.81 | 1.01 |

It is seen from the data in Table 7 that there is a significant failure at about 100° C. in adhesion of the bracket samples that had been irradiated with UVA light relative to the non-UVA-irradiated control samples.

Example 9

DMA Evaluation of Hardened CHDVEDMA/HEMA/Sulfonium Salt Strips

In order to demonstrate the photothermal sensitivity property of CHDVEDMA in the presence of an in-situ generated photoacid, a hardened composite strip containing CHDVEDMA was prepared, subjected to UVA irradiation, and subjected to Dynamic Mechanical Analysis (DMA) according to the following procedure.

A liquid composition of CHDVEDMA (48.6 wt.-%), HEMA (45.1 wt.-%), $Ar_3S^+$ $PF_6^-$ (5.7 wt.-%), and IRGACURE 819 (0.6 wt.-%) was prepared by mixing the combined components in an ultrasonic bath at room temperature for 5 minutes.

Hardened strips of the composition were prepared by pouring the solution into a mold and irradiating by exposure to UVA at room temperature using a medium pressure Hg spot cure lamp (100 W, Super Spot Max, Lesco, Torrance, Calif.) fitted with a long-pass 420-nm interference filter (GG420 filter; Esco Products, Oak Ridge, N.J.) at the tip of the optical fiber. The strips were 5 mm (wide)×0.45 mm (thick)×15 mm (length). One Control Strip was without any UV exposure whereas another strip was exposed to UVA for 120 seconds at a distance of 3 cm from the tip of the optical fiber. The strips were subjected to DMA analysis as follows:

The analysis was carried out on a Model Q800 v. 3.13 Build 74 DMA instrument (TA Instruments, New Castle, Del.). The strips were subjected to a 0.1% oscillatory strain while ramping from room temperature to 250° C. at 2° C./min. A static force of 0.05N was applied during the course of the entire run and the minimum oscillatory force was set to $10^{-5}$ N. The Force Track feature available in this instrument was set to 125%. Data were collected at 1 point every second.

The DMA results demonstrated that the onset of loss of storage modulus in the UVA-exposed strip (containing generated photoacid) was about 50° C. and the loss was complete at about 180° C. with a sharp, sudden drop. In contrast, the onset of loss of storage modulus in the Control Strip (no UVA exposure, and thus containing no photoacid) was about 125° C. and the loss of modulus was incomplete even at 250° C.

Example 10

Photobonding and Photothermal (100° C.) Debonding on Glass Using an Adhesive Containing CHDVEDMA/HEMA/IRGACURE/Sulfonium Salt In order to demonstrate the photobonding (i.e., bonding after exposure to radiation) and photothermal debonding properties of adhesives containing CHDVEDMA, an adhesive coating containing CHDVEDMA was prepared and photochemically cured to adhere an orthodontic bracket to a glass slide. The adhered bracket was subjected to sequential UVA irradiation and heat, and shear bond strengths determined. These procedures were carried out as follows.

A liquid adhesive composition of CHDVEDMA (46.7 wt.-%), HEMA (46.8 wt.-%), $Ar_3S^+$ $PF_6^-$ (5.6 wt.-%), and IRGACURE 819 (0.9 wt.-%) was prepared by mixing the combined components in an ultrasonic bath at room temperature for 5 minutes.

Window glass slides (3-mm thickness) were cleaned with methanol just prior to use. Approximately 10 mg of the adhesive composition was placed on the non-fluorescent side of the cleaned slide as a single drop. A TRANSCEND 6000 ceramic bracket (Part No. 59543-01, 3M Unitek, Monrovia, Calif.) was placed into the drop of adhesive formulation and bonding was carried out by irradiation through the underside of the glass slide using the Lesco Super Spot Max fiber optic light source (1.4 cm from the glass slide) fitted with the long-pass 420-nm Esco GG420 filter for 30 seconds. This was repeated for 2 sets of 6 TRANSCEND 6000 brackets.

For the debonding experiments, one set of 6 bonded brackets was exposed to radiation from the Lesco light source fitted with the 420-nm Esco filter for 2×30 seconds with a 30-second interval (ie, Control Brackets with no UVA exposure). The other set of 6 bonded brackets was exposed to radiation from the Lesco light source without the Esco filter for the same time duration (ie, Test Brackets with UVA exposure at longer than 300 nm). Bond strengths of both sets of brackets were then determined following exposure to a temperature of 100° C. according to the Shear Bond Strength on Glass Test Method B described herein. Results are shown in Table 8 for 6 replicates at the two different levels of exposure of UVA irradiation (i.e., no UVA, and UVA exposure for 2×30 seconds) plus an average result for each level.

TABLE 8

Debonding of Ceramic Brackets from Glass Surface.
Bond Strength (MPa) after 100° C. Exposure

| Run | No UVA | 2 × 30 sec UVA |
| --- | --- | --- |
| 1 | 9.33 | 0.31 |
| 2 | 6.44 | 0.11 |
| 3 | 6.86 | 0.15 |
| 4 | 8.89 | 0.15 |
| 5 | 7.63 | 0.10 |
| 6 | 6.99 | 0.10 |
| Average: | 7.69 | 0.15 |

It is seen from the data in Table 8 that there is a significant failure (after 100° C. exposure) in adhesion of the UVA-irradiated Test Brackets relative to the non-UVA-irradiated Control Brackets. The Control Brackets that were irradiated with only visible light (no UVA) showed mixed failure in that they had adhesive failure at the bracket as well as the glass surface. The Test Brackets that were irradiated with UVA failed purely at the glass-adhesive interface.

Example 11

Photobonding and Photothermal (70° C.) Debonding on Glass Using an Adhesive Containing CHDVEDMA/HEMA/IRGACURE/Sulfonium Salt A liquid adhesive composition of CHDVEDMA (46.7 wt.-%), HEMA (46.1 wt.-%), $Ar_3S^+ PF_6^-$ (6.2 wt.-%), and IRGA-CURE 819 (0.9 wt.-%) was prepared by mixing the combined components in an ultrasonic bath at room temperature for 5 minutes.

Window glass slides (3-mm thickness) were cleaned with methanol just prior to use. Approximately 10 mg of the adhesive composition was placed on the non-fluorescent side of the cleaned slide as a single drop. A TRANSCEND 6000 ceramic bracket (Part No. 59543-01, 3M Unitek) was placed into the drop of adhesive formulation and bonding was carried out by irradiation through the underside of the glass slide using the Lesco Super Spot Max fiber optic light source (1.5 cm from the glass slide) fitted with the long-pass 420-nm Esco GG420 filter for 2×30 seconds with a 30-second interval. This was repeated for 2 sets of 10 TRANSCEND 6000 brackets.

For the debonding experiments, one set of 10 bonded brackets was exposed to radiation from the Lesco light source fitted with the 420-nm Esco filter for 30 seconds (ie, Control Brackets with no UVA exposure). The other set of 10 bonded brackets was exposed to radiation from the Lesco light source without the Esco filter for the same time duration (ie, Test Brackets with UVA exposure at longer than 300 nm). Bond strengths of both sets of brackets were then determined following exposure to a temperature of 100° C. according to the Shear Bond Strength on Glass Test Method C described herein. Results are shown in Table 9 for 10 replicates at the two different levels of UVA irradiation (i.e., no UVA, and UVA exposure for 30 seconds) plus an average result for each level.

TABLE 9

Debonding of Ceramic Brackets from Glass Surface. Bond Strength (MPa) after 70° C. Exposure

| Run | No UVA | 30 sec UVA |
|---|---|---|
| 1 | 4.86 | 0.21 |
| 2 | 6.80 | 0.82 |
| 3 | 6.32 | 1.78 |
| 4 | 5.59 | 0.21 |
| 5 | 6.71 | 0.75 |
| 6 | 5.23 | 1.12 |
| 7 | 8.77 | 0.99 |
| 8 | 6.14 | 0.38 |
| 9 | 5.96 | 0.70 |
| 10 | 7.64 | 0.29 |
| Average: | 6.40 | 0.72 |

It is seen from the data in Table 9 that there is a significant failure (after 70° C. at 3 minutes exposure) in adhesion of the UVA-irradiated Test Brackets relative to the non-UVA-irradiated Control Brackets. The Control Brackets that were irradiated with only visible light (no UVA) showed mixed failure in that they had adhesive failure at the bracket as well as the glass surface with the most failing at the bracket. The Test Brackets that were irradiated with UVA failed purely at the glass-adhesive interface.

Example 12

Photobonding and Photothermal Debonding on Teeth Using an Adhesive Containing CHDVEDMA/HEMA/IRGACURE/Sulfonium Salt/NIR-Absorber In order to demonstrate the photobonding and photothermal debonding properties of adhesives containing CHDVEDMA, a silica-filled orthodontic adhesive coating containing CHDVEDMA was prepared and photochemically cured to adhere orthodontic brackets to bovine teeth surfaces. The adhered brackets were subjected to sequential UVA light irradiation and heated (generated by white-light irradiation of the near infrared (NIR)-absorber present in the adhesive), and shear bond strengths determined. These procedures were carried out as follows.

A liquid adhesive composition (Example 12) of CHDVEDMA (26.5 wt.-%), HEMA (26.5 wt.-%), $Ar_3S^+ PF_6^-$ (3.3 wt.-%), IRGACURE 819 (0.6 wt.-%), SO-E2 Filler (39.9 wt.-%), and TRB SH 7080 (3.3 wt.-%) was prepared by mixing the combined components in an DAC-150 Speed-Mixer (manufactured by Hauschild & Co, Hamm, Germany and distributed by FlackTek, Inc., Landrum, S.C.) at room temperature for 3×1 minutes.

Nine bovine teeth were potted in a poly(methyl methacrylate) base, dried with a stream of dry air, and were etched and primed using ADPER PROMPT L-Pop self-etching adhesive (3M ESPE, St. Paul, Minn.) for 10 seconds followed by blowing with a stream of air to remove excess adhesive. Approximately 10 mg of the orthodontic adhesive formulation was placed on a treated tooth surface. A TRANSCEND 6000 ceramic bracket (Part Nos. 59543-01, 3M Unitek) was carefully placed onto the adhesive formulation and bonding was carried out by irradiating all nine bracket samples with a Lesco Super Spot Max light source fitted with a 420-nm long pass filter (GG 420, Esco Products). Irradiation was carried out two times for 15 seconds with a 30-second interval.

For the debonding experiments, five of the bonded bracket samples (Controls) were irradiated by exposure for 6×10 seconds to the same LESCO Super Spot Max light source (fitted with the 420-nm long pass GG 420 filter; thus, to mimic the heat provided from the light source, but without UVA light). Four of the bonded brackets (Test Samples) were irradiated by exposure for 6×10 seconds to UVA light using the same LESCO Super Spot Max light source (but without the filter). There was a 30-second interval between each irradiation period for a given tooth to avoid overheating. As a result four bonded brackets were UV-activated and five bonded brackets were not. Bond strengths were then determined at about 100° C. according to the Shear Bond Strength on Teeth Test Method B described herein.

Results are shown in Table 10 for 4-5 replicates at the two different levels of UVA irradiation (i.e., no UVA, and UVA exposure for 6×10 seconds) plus an average result for each level.

TABLE 10

Debonding of Ceramic Brackets from Teeth Surfaces.
Bond Strength (MPa) after about 100° C. Exposure

| Run | No UVA | 6 × 10 sec UVA |
|---|---|---|
| 1 | 5.58 | 2.51 |
| 2 | 5.36 | 2.59 |
| 3 | 3.82 | 3.71 |
| 4 | 7.67 | 3.85 |
| 5 | 6.94 | — |
| Average: | 5.87 | 3.16 |

It is seen from the data in Table 10 that there is a significant failure (after visible-light induced heating) in adhesion of the UVA-irradiated Test Brackets relative to the non-UVA-irradiated Control Brackets. The failure mode for all brackets (Control Brackets and Test Brackets) was cohesive.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for reducing the bond strength of an orthodontic appliance adhered to a tooth structure with a hardened dental composition, the method comprising irradiating the hardened dental composition, wherein the hardened dental composition comprises an acid-generating component and an acid-reactive component that comprises one or more acid-reactive groups.

2. The method of claim 1 wherein irradiating the hardened dental composition results in the acid-generating component generating an acid that reacts with greater than a stoichiometric amount of the one or more acid-reactive groups.

3. The method of claim 2 wherein the acid-generating component comprises a sulfonium salt, and optionally a sensitizer.

4. The method of claim 3 wherein irradiating comprises irradiating with ultraviolet A radiation and/or visible radiation.

5. The method of claim 1 wherein the acid-reactive component is formed by polymerizing one or more compounds including a compound selected from the group consisting of: compounds represented by the formula (Formula I):

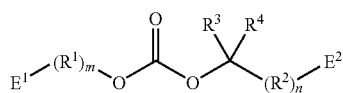

wherein $R^1$ and $R^2$ each independently represent an organic group; $R^3$ and $R^4$ each independently represent hydrogen or an organic group, with the proviso that only one of $R^3$ and $R^4$ can be hydrogen; each $E^1$ and $E^2$ independently represents an ethylenically unsaturated group; and m and n are each independently 0 or 1, and wherein $R^1$ and $E^1$ can optionally be combined to form one or more rings and/or two or more groups among $R^2$, $R^3$, $R^4$, and $E^2$ can optionally be combined to form one or more rings;

compounds represented by the formula (Formula II):

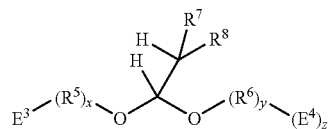

wherein $R^5$, $R^6$, $R^7$, and $R^8$ each independently represent an organic group; each $E^3$ and $E^4$ independently represents an ethylenically unsaturated group; and x, y, and z are each independently 0 or 1, with the proviso that if z=0, then at least one of $R^7$ and $R^8$ represents an ethylenically unsaturated group, with $R^5$ and $R^6$ being selected to allow for, upon exposure to acid, preferential cleavage from the acetal of the oxygen atom attached to $R^5$ over the oxygen atom attached to $R^6$; and wherein two or more of $R^5$, $R^6$, $R^7$, $R^8$, $E^3$, and/or $E^4$ can optionally be combined to form one or more rings, with the proviso that the one or more rings do not interfere with the ability of the acid-reactive group to form two or more separate groups upon reaction with acid; and
combinations thereof 6. The method of claim 1 further comprising heating at least a portion of the irradiated hardened dental composition to at least 42° C.

7. The method of claim 1 wherein the hardened dental composition is a hardened primer, and the orthodontic appliance is further adhered to a primed tooth structure with a hardened orthodontic adhesive.

8. The method of claim 7 further comprising removing the orthodontic appliance from the tooth structure, wherein the hardened orthodontic adhesive is substantially retained on the removed orthodontic appliance.

9. A method for reducing the adherence of a hardened dental composition to a tooth structure, the method comprising irradiating the hardened dental composition to reduce the adherence, wherein the hardened dental composition comprises an acid-generating component and an acid-reactive component comprising one or more acid-reactive groups.

10. A method for reducing the bond strength of an orthodontic appliance adhered to a tooth structure with a hardened dental composition, the method comprising:
irradiating the hardened dental composition; and
subsequently heating the irradiated hardened dental composition, resulting in a reduced bond strength.

11. The method of claim 10 wherein the hardened dental composition comprises a radiation-to-heat converter, and heating comprises irradiating the hardened dental composition.

12. A hardenable dental composition comprising:
a hardenable component comprising one or more acid-reactive groups; and
an acid-generating component, wherein the hardenable component comprising the one or more acid-reactive groups is selected from the group consisting of:
compounds represented by the formula (Formula I):

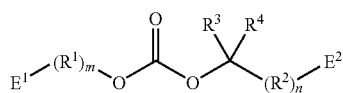

wherein $R^1$ and $R^2$ each independently represent an organic group; $R^3$ and $R^4$ each independently represent hydrogen or an organic group, with the proviso that only one of $R^3$ and $R^4$ can be hydrogen; each $E^1$ and $E^2$ independently represents an ethylenically unsaturated group; and m and n are each independently 0 or 1, and wherein $R^1$ and $E^1$ can optionally be combined to form one or more rings and/or two or more groups among $R^2$, $R^3$, $R^4$, and $E^2$ can optionally be combined to form one or more rings;

compounds represented by the formula (Formula II):

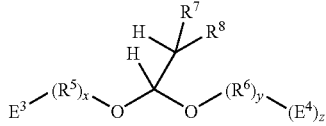

wherein $R^5$, $R^6$, $R^7$, and $R^8$ each independently represent an organic group; each $E^3$ and $E^4$ independently represents an ethylenically unsaturated group; and x, y, and z are each independently 0 or 1, with the proviso that if z=0, then at least one of $R^7$ and $R^8$ represents an ethylenically unsaturated group, with $R^5$ and $R^6$ being selected to allow for, upon exposure to acid, preferential cleavage from the acetal of the oxygen atom attached to $R^5$ over the oxygen atom attached to $R^6$; and wherein two or more of $R^5$, $R^6$, $R^7$, $R^8$, $E^3$, and/or $E^4$ can optionally be combined to form one or more rings, with the proviso that the one or more rings do not interfere with the ability of the acid-reactive group to form two or more separate groups upon reaction with acid; and combinations thereof.

13. An orthodontic appliance having a base for bonding the appliance to a tooth structure; and a hardenable dental composition on the base of the appliance, wherein the hardenable dental composition comprises:
an acid-generating component;
a hardenable component comprising one or more acid-reactive groups; and
an initiator for initiating the hardening of the hardenable dental composition, wherein the hardenable component comprising the one or more acid-reactive groups is selected from the group consisting of:
compounds represented by the formula (Formula I):

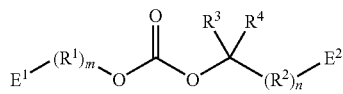

wherein $R^1$ and $R^2$ each independently represent an organic group; $R^3$ and $R^4$ each independently represent hydrogen or an organic group, with the proviso that only one of $R^3$ and $R^4$ can be hydrogen; each $E^1$ and $E^2$ independently represents an ethylenically unsaturated group; and m and n are each independently 0 or 1, and wherein $R^1$ and $E^1$ can optionally be combined to form one or more rings and/or two or more groups among $R^2$, $R^3$, $R^4$, and $E^2$ can optionally be combined to form one or more rings;

compounds represented by the formula (Formula II):

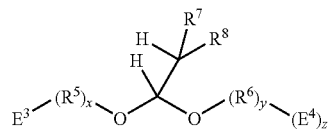

wherein $R^5$, $R^6$, $R^7$, and $R^8$ each independently represent an organic group; each $E^3$ and $E^4$ independently represents an ethylenically unsaturated group; and x, y, and z are each independently 0 or 1, with the proviso that if z=0, then at least one of $R^7$ and $R^8$ represents an ethylenically unsaturated group, with $R^5$ and $R^6$ being selected to allow for, upon exposure to acid, preferential cleavage from the acetal of the oxygen atom attached to $R^5$ over the oxygen atom attached to $R^6$; and wherein two or more of $R^5$, $R^6$, $R^7$, $R^8$, $E^3$, and/or $E^4$ can optionally be combined to form one or more rings, with the proviso that the one or more rings do not interfere with the ability of the acid-reactive group to form two or more separate groups upon reaction with acid; and combinations thereof.

14. An orthodontic appliance having a base for bonding the appliance to a tooth structure; and a hardened dental composition on the base of the appliance, wherein the hardened dental composition comprises an acid-generating component and an acid-reactive component comprising one or more acid-reactive groups; and one or more additional layers of different hardenable and/or hardened dental compositions.

15. A method for bonding an orthodontic appliance to a tooth, the method comprising:
providing a precoated orthodontic appliance having a base for bonding the appliance to a tooth structure, wherein the appliance includes a hardened dental composition comprising an acid-generating component and an acid-reactive component on the base thereof and a hardenable orthodontic adhesive on the hardened dental composition;
applying the base of the appliance having the hardenable orthodontic adhesive on the hardened dental composition thereon to the tooth structure; and
hardening the orthodontic adhesive, wherein the precoated appliance further comprises one or more additional layers of different hardenable and/or hardened dental compositions.

* * * * *

UNITED STATES PATENT AND TRADEMARK OFFICE
CERTIFICATE OF CORRECTION

PATENT NO. : 7,776,940 B2
APPLICATION NO. : 11/275238
DATED : August 17, 2010
INVENTOR(S) : Rajdeep S. Kalgutkar Page 1 of 2

It is certified that error appears in the above-identified patent and that said Letters Patent is hereby corrected as shown below:

Title Page; item (56); Page 3, Col. 2, OTHER PUBLICATIONS
Line 3, Delete "Mateirals" and insert -- Materials --, therefor.

Column 2
Line 25, Delete "applicances" and insert -- appliances --, therefor.

Column 6
Line 41, Delete "phenothiazene" and insert -- phenothiazine --, therefor.

Column 12
Line 63, Delete "bisphenolA" and insert -- bisphenol A --, therefor.

Column 13
Line 64, Delete "Ethythylenically" and insert -- Ethylenically --, therefor.

Column 18
Line 17, Delete "ie.," and insert -- i.e., --, therefor.

Column 20
Line 23, Delete "tetrafluoroboarate." and insert -- tetrafluoroborate. --, therefor.

Column 23
Line 43, Delete "thereof" and insert -- thereof. --, therefor.

Column 25
Line 46, Delete "Thermallylabile" and insert -- Thermally Labile --, therefor.

Column 26
Line 47, Delete "0.01" and insert -- 0.01% --, therefor.

Signed and Sealed this

Thirtieth Day of November, 2010

David J. Kappos
*Director of the United States Patent and Trademark Office*

Column 27
Line 61, Delete "Schiff's" and insert -- Schiff's --, therefor.

Column 28
Line 18, Delete "microcystalline" and insert -- microcrystalline --, therefor.

Column 29
Line 33, Delete "squarilium" and insert -- squarylium --, therefor.

Column 39
Line 1, Delete "Preparatrions" and insert -- Preparations --, therefor.
Line 9, Delete "of2" and insert -- of 2 --, therefor.

Column 40
Line 3, Delete "andpurification" and insert -- and purification --, therefor.

Column 50
Line 1, Delete "with the" and insert -- with --, therefor.
Line 20, Delete "heated" and insert -- heat --, therefor.

Column 52
Line 23, In Claim 5, Delete "thereof" and insert -- thereof. --, therefor.